United States Patent [19]
Ham et al.

[11] Patent Number: 5,553,616
[45] Date of Patent: Sep. 10, 1996

[54] DETERMINATION OF CONCENTRATIONS OF BIOLOGICAL SUBSTANCES USING RAMAN SPECTROSCOPY AND ARTIFICIAL NEURAL NETWORK DISCRIMINATOR

[75] Inventors: Fredric M. Ham; Glenn M. Cohen, both of Indialantic, Fla.

[73] Assignee: Florida Institute of Technology, Melbourne, Fla.

[21] Appl. No.: 160,033

[22] Filed: Nov. 30, 1993

[51] Int. Cl.$^6$ .................................................. A61B 5/00
[52] U.S. Cl. ........................... 128/633; 128/634; 395/25; 395/924; 250/339.07; 250/341.1
[58] Field of Search ................................. 128/633, 634, 128/664, 665; 250/339, 340, 341, 339.01, 339.07, 340, 339.09, 341.1, 341.5; 395/21, 23, 24, 25, 924; 356/39, 301

[56] References Cited

U.S. PATENT DOCUMENTS

| | | | |
|---|---|---|---|
| 4,679,426 | 7/1987 | Fuller et al. | 73/53 |
| 4,718,417 | 1/1988 | Kittrell et al. | 128/634 |
| 4,765,179 | 8/1988 | Fuller et al. | 73/53 |
| 4,975,581 | 12/1990 | Robinson et al. | 128/633 |
| 5,099,123 | 3/1992 | Harjunmaa | 250/345 |
| 5,137,023 | 8/1992 | Mendelson et al. | 128/633 |
| 5,183,042 | 2/1993 | Harjunmaa et al. | 128/655 |
| 5,280,792 | 1/1994 | Leong et al. | 128/702 |
| 5,293,872 | 3/1994 | Alfano et al. | 128/664 |
| 5,303,026 | 4/1994 | Strobl et al. | 128/665 |
| 5,339,818 | 8/1994 | Baker et al. | 128/680 |

OTHER PUBLICATIONS

"An Idea Whose Time Has Come?" by Shauna S. Roberts; *Diabetes Forecast*, May, 1993; pp. 25–27.

*Primary Examiner*—Ruth S. Smith
*Attorney, Agent, or Firm*—Charles E. Wands

[57] ABSTRACT

The concentration of a substance, such as glucose, in a biological sample, such as human tissue (e.g. the skin of an index finger) is non-invasively determined by directing the output beam of a laser diode onto and into the skin so as to cause Raman scattering. The output of a charge coupled device, upon which the scattered light is spatially dispersed according to frequency is digitized and applied to a processor. The processor compares the Raman scattering intensity characteristics of the sample with a comparative model, in particular, an artificial neural network discriminator (ANND). The ANND is trained with a plurality of Raman spectral characteristics from biological fluids or tissue, possessing known Raman scattered light intensities versus wavelength characteristics at known concentrations. A preferred implementation of the ANND employs fuzzy adaptive resonance theory-mapping (ARTMAP), which has robust noise rejection capabilities and can readily handle nonlinear phenomena.

2 Claims, 12 Drawing Sheets

DETERMINATION OF CONCENTRATIONS OF BIOLOGICAL SUBSTANCES USING RAMAN SPECTROSCOPY AND ARTIFICIAL NEURAL NETWORK DISCRIMINATOR

FIELD OF THE INVENTION

The present invention relates in general to primarily biological substance analysis and, in particular, to a method and apparatus for non-invasively determining the concentrations of a biological substance, such as glucose, by processing electro-optic signals obtained by Raman scattering by means of an artificial neural network discriminator.

BACKGROUND OF THE INVENTION

To properly care for human subjects, as well as animals, it is necessary to ascertain information pertaining to concentrations of certain blood constituents, and other body fluids. For example, diabetics must periodically monitor their blood glucose, sometimes as often as several times daily. This information is necessary, so that insulin adjustments can be made to facilitate control of diabetes mellitus. According to a position statement of the American Diabetes Association in an article published in Clinical Diabetes, Volume 11, Number 4, pages 91–96, entitled: "Implications of the Diabetes Control and Complications Trial," tight control, or intensive therapy, could reduce many of the problems associated with diabetes mellitus. If proper monitoring of blood glucose and resultant insulin adjustments are not carried out, many physiological problems can occur for the diabetic patient.

Among problems that can occur are diabetic ketoacidosis, hyperosmolar hyperglycemia non-ketotic coma, and hypoglycemia. More devastating chronic developments include microvascular, neuropathic, and macrovascular disorders leading to blindness, renal failure, limb amputation, heart disease and stroke. Some of these problems can occur even with strict adherence to diet, exercise, blood glucose monitoring with current monitoring systems, and insulin replacement.

Major reasons that can account for these problems include the fact that blood glucose must be monitored as often as necessary to provide tight control of large insulin-glucose fluctuations (hypoglycemia-hyperglycemia), as described, for example, in an article entitled "Diabetes Patient Education Programs," by M. Wheeler et al, Diabetes. Care, Vol. 15, Supl.1, pp 36–40, 1992. An unfortunate impediment to the lack of patient adherence to proper monitoring is that fact that current methods to monitor blood glucose require a finger prick, which can be painful and can precipitate the contraction of infectious diseases. Due to lack of patient adherence (causes may include fear of finger prick, forgetfulness, apathy) blood glucose monitoring may not be conducted at the proper frequency, as described in an article by R. Surwit et al., entitled "The Role of Behavior in Diabetes Care," Diabetes Care. Vol. 5, No. 3, pgs. 337–342, 1982.

In addition, Type I diabetics can experience abrupt fluctuations in glucose concentrations during the intervals between scheduled tests despite their strict adherence to proper diet, exercise, and insulin replacement. Further, in some cases with certain types of home blood glucose monitoring systems, inaccurate readings can occur. (See, for example, an article by V. Laus et al., entitled: "Potential Pitfalls in the Use of Glucoscan and Glucoscan II Meters for Self-monitoring of Blood Glucose", Diabetes Care. Vol. 7, pgs. 590–594, 1984.)

Such fluctuations between test intervals underscore the need for the development of a non-invasive glucose monitoring sensor that can be used as often as medically needed, even continuously. (Some Type II diabetics must monitor their blood glucose levels on a daily basis, and timely and precise monitoring of blood glucose will improve the health of diabetics and improve their quality of life by reducing the long-term effects of the disease.)

A variety of systems have been proposed to monitor blood glucose non-invasively. For example, the Kaiser U.S. Pat. No. 4,169,676, describes a system for determining of blood glucose concentration by irradiating biological fluids with a $CO_2$ (carbon dioxide) laser. The laser beam is coupled to the sample by way of an attenuated total reflectance (ATR) prism. Kaiser describes that using a laser source in infrared (IR) spectroscopy provides an improvement of about one hundred times in measurement sensitivity over conventional techniques, and a monochromatic laser source considerably improves the resolution. However, even with improved resolution and sensitivity, this method basically relies on using single wavelength 'absorption' intensity data to determine varying concentrations of blood glucose. No consideration is given to interactions with other substances, and how such interactions may interfere with concentration measurements. As a consequence, this approach, using a single wavelength (or univariate analysis), yields highly unreliable results. In addition, a $CO_2$ laser source is impractical because of its bulky size and because it generates unsafe amounts of heat for clinical use.

The Muller U.S. Pat. No. 4,427,889, describes a mechanism for determining blood glucose concentrations that utilizes a single beam laser operating at two wavelengths in the mid-infrared (IR) region to irradiate a multi-component sample, selected from whole blood or urine. The first measured wavelength lies within the infrared spectral range of 10.53 to 10.64 microns, and the second wavelength lies between 9.13 to 9.17 microns. The measurement is standardized by forming the ratio of 'absorption' values of the first and second wavelengths. Glucose concentration is proportional to the absorption value that is measured at the second wavelength, while there is no glucose absorption at the first wavelength which provides a baseline absorption for the sample. Unfortunately, this approach has the same basic problem as the Kaiser scheme, described above.

The Dahne et al U.S. Pat. No. 4,655,225, uses near-IR spectroscopy for non-invasive determination of blood glucose (or glucose in tissues). A near-IR source in the 1000 to 2500 nm range is used to transmit light 'through' a finger or earlobe. The patentees also describe a method for analyzing near-IR energy that is diffusely reflected from 'deep within' the irradiated tissue. Spectroscopic responses are taken at two different wavelengths to quantify glucose. One wavelength is used to establish background absorption, while the other is used for determining glucose absorption. Concentrations of glucose are determined from the ratio of the two wavelengths. As in the case of Muller and Kaiser, this approach is not reliable because it relies on univariate analysis.

The Robinson et al U.S. Pat. No. 4,975,581, describes a technique to quantify glucose concentrations through the use of both a mid-IR light source using an ATR crystal and a broad-spectrum near-IR light source (having a wavelength on the order of 500 to 1000 nm). The patentees acknowledge the need for multivariate analysis to improve analysis precision over univariate analysis. This is accomplished by comparing the similarity of multiple wavelengths of IR energy obtained from an irradiated sample to that of a calibration model, obtained by the methods of partial least squares and principal component regression (chemometric analysis). The calibration model employed by Robinson et al. is a function of the concentration of materials in known samples as a function of absorption at several wavelengths of infrared energy.

Although the Robinson et al. '581 patent also acknowledges the importance of identifying and removing outlier samples from the calibration set, an outlier category of importance is not necessarily one of anomalies associated with instrumentation, positioning of the finger in the instrument, etc., but may result from insufficient calibration of the comparative model due to, for example, molecular interactions that have not previously been considered during model calibration. In the latter case, outlier data is essential for further "tuning" of the model to increase accuracy and precision. Removal of the outlier data, as opposed to utilizing it for model "tuning" would actually degrade the instrument's accuracy and precision. Therefore, concentration decisions based on a chemometric calibration model may not yield robust results. Also, the use of photodiode array elements in the Robinson et al patent does not take advantage of the capabilities of other detector array systems to remove noise. The responsivity of photodiode elements is less than those used in other detector array systems.

They also overlook fundamental principles of the optical properties of skin. For example, studies reported in an article by Hardy et al, entitled "Spectral Transmittance and Reflectance of Excised Human Skin", Journal of Applied Physics, Vol. 9, pp 257–264, 1956, which describes measurements of transmission and remission of an incident beam through skin samples of various thicknesses, including both the epidermis and various amounts of dermis, reveal that, as the thickness of the dermis increases, transmission decreases, and becomes more diffuse, suggesting multiple scattering, as described by R. Anderson et al, in "Optical Properties of Human Skin", The Science of Photomedicine, Plenum Press, N.Y., pgs. 147–194, 1982. From studies such as these, it was determined that the Lambert-Beer law is invalid for visible and NIR (near-infrared) wavelengths, when skin thickness exceeds 0.5 mm, which leads to nonlinear results that must be accounted for and corrected.

In an article entitled "Non-invasive Glucose Monitoring in Diabetic Patients: A Preliminary Evaluation", by Robinson et al., Clinical Chemistry, Vol. 38 No. 9, 1992, pp 1618–1622, the authors state that the "relative predictive abilities of these methods were examined in detail for the situation when Beer's law is followed. However, in complex analyses, such as studies here, that involve non-linearities and other deviations from ideal behavior, we do not fully understand these differences in performance."

The ability of any signal processing technique to extract information from spectroscopic data for determination of glucose concentrations relies heavily on the processes capability to account for nonlinearities, such a nonlinearities which can result from light penetrating skin at depths greater than 0.5 mm. Other sources of nonlinear relationships between spectral response and analyte concentrations can occur as a result of the instrumentation used, inter-constituent interactions, detector nonlinearities, etc. In the case of the above-identified '581 Robinson et al. patent, the use of chemometric calibration models (partial least squares and principal component regression) these nonlinearities cannot be totally accounted for by using linear models to fit nonlinear data. They will provide adequate results only if the nonlinear data is "linear" over a small region. However, this is not guaranteed to be the case, and therefore erroneous data can occur which will result in improper prediction of glucose concentrations. In an article recently published by P. J. Gemperline, et al entitled "Nonlinear Multivariate Calibration Using Principal Components Regression and Artificial Neural Networks," Analytical Chemistry, Vol. 63, No. 20, 1991 pp. 2313–2323 and an article published by P. Bhandare et al entitled "Multivariate Determination of Glucose in Whole Blood Using Partial Least-Squares and Artificial Neural Networks Based on Mid-Infrared Spectroscopy", Applied Spectroscopy, Vol, 47, No. 8, 1993, pp. 1214–1221, principal component regression (PCR) with an artificial neural network and partial least squares (PLS) with an artificial neural network, respectively, were used for detecting and modeling nonlinear regions of spectral response in multivariate, multi-component spectroscopic assays and determination of glucose concentrations, respectively. Although, these researchers claim improved results over the standard chemometric methods, they are continuing to use linear models for the nonlinear data. Their use of PCR and PLS techniques is for the purpose of signal characterization, i.e. feature extraction or data compression, such that, the reduced data sets which results are used as exemplars which are in turn used as inputs to the artificial neural networks. However, the same problems can occur with these approaches as can occur with the PCR and PLS techniques alone, that is, they are using linear models to fit nonlinear data. The resultant extracted features based on these linear modeling techniques are then presented to the non-linear artificial neural network.

Another major problem associated with the use of partial least squares (PLS) and principal component regression (PCR) spectral modeling techniques, as used by Robinson et al., is the determination of the number of factors that must be retained in order to yield the best results. Too many, or too few, factors can lead to improper calibration in the modeling process. Also, there is no evidence of compensation for temperature variations that will occur in vivo and in vitro. Absorption spectroscopy can be very sensitive to variations in temperature.

The Rosenthal et al. U.S. Pat. No. 5,086,229, describes a number of scenarios which use one or more infrared emitting diodes (IRED) as a light source(s), with one or more photodetectors. Multivariate analysis is also employed. However, the spectral regions used to collect absorbance data appear to be selected such that absorbance contributions due to water are minimized without regard to maximizing spectral intensities with respect to glucose, using for example a comparative model calibrated by use of spectroscopic absorbance data at various wavelengths associated with glucose spectral characteristics and other inferring analytes. The spectra shown in FIG. 15 of their patent are referred to as the effective spectra of glucose in the human body. The effective spectra were determined by subtracting two spectra obtained by transmitting optical energy having a wavelength between 600 nm to 1100 nm, in 1 nm intervals, 'through' the distal portion of an index finger. The resultant effective spectra are those associated with glucose and other reference substances. Therefore, the information which is sought, that is, the spectral intensities associated with glucose that can be related to various concentrations, are 'buried' in the overall spectral distribution.

Since glucose metabolism involves a complex interplay of hormones, spectral intensities of certain other substances, which can have wavelength characteristics in this spectral region, will change in response to glucose metabolism. Therefore, intensity variations in this spectral region at certain wavelengths of interest, which are observed as glucose is metabolized, can change as a result of the presence of many other substances, such as those in protein and lipid metabolism, and not glucose alone. This complex system and its molecular interactions may also account in part for their inconclusive clinical tests. Also, in the Rosenthal et al scheme, normalized derivative analysis of data obtained at multiple wavelengths, surrounding infrared spectral peaks and troughs which are produced by the presence of glucose and other reference substances, is employed to relate changes in concentrations of glucose to changes in absorbance.

Although the derivative technique can offer the advantage of ascertaining more precisely the center of each absorbance peak, the use of derivative techniques, without prior sophisticated signal processing of the data to reduce noise, can lead to an enhancement of the noise as well as the signal of interest. This might have contributed to inconclusive clinical tests that were performed in 1991. Therefore, a well-defined decision-based approach is not readily apparent in their scheme/approach for determining glucose concentrations. Rosenthal et al. state that an instrument can be constructed which provides accurate blood glucose measurements, which would have to correct for inaccuracies resulting for each person's "wavelength uniqueness." This is an acknowledgment of the aforementioned problem, but there does not appear a viable approach to overcome it.

Correcting inaccuracies for each individual in this manner does not establish a stable baseline which would be constant over time. With a 'user-customized' instrument approach, inaccurate calibrations could lead to erroneous glucose concentration readings. This unreliable information would in turn be used by diabetic patients for insulin adjustments. As with the approach described by Robinson et al, referenced above, Rosenthal et al also overlook fundamental principles of the optical properties of skin.

In summary, all of the above-described prior art techniques are unique in terms of the methods used to determine glucose concentrations. However, they all have a common problem associated with them. Those methods which extract spectroscopic data to determine concentrations of glucose, which are buried in an effective infrared spectrum, are not reliable, and thus do not produce repeatable results. The spectral information of glucose that must be extracted from the effective spectrum not only has other spectra which can overlap the glucose spectrum, but the spectral characteristics associated with glucose alone can be altered by molecular interactions with other analytes (inter-constituent interactions). This includes the effects of hydrogen bonding and matrix effects caused by materials used in the instrument that come into contact with body fluids or tissue. (See, for example, an edited conference paper by W. Miller et al., entitled "Matrix Effects and Accuracy Assessment in Clinical Chemistry", Archives of Pathology & Laboratory Medicine, Vol. 117, No. 4, pgs. 343–436, 1993.) These techniques also do not fully address the non-linear effects than can occur in this type of process.

Also, the near-IR spectral region is essentially featureless and has the disadvantage of low absorbance by organic substances compared to absorbencies in the mid-IR region. However, using an irradiating source in the mid-IR spectral region and detecting resulting absorbencies in the same spectral region has the problem of requiring a special detector which must be cooled with liquid nitrogen in order to obtain necessary sensitivity. In addition, penetration depths of mid-IR energy are limited compared to those obtained when a near-IR source is used. Also, using a mid-IR source and measuring spectral characteristics in the near-IR spectrum, which are overtones and combination bands of spectral features in the mid-IR region, are not necessarily advantageous, because the overtones and combination bands have an extremely low intensity compared to the fundamental frequency intensities in the mid-IR for glucose.

Other prior art techniques to determine concentrations of biological substances in body fluids use chemical, enzymatic, and/or immunological methods. These methods require invasive means either to draw blood for analysis or to implant the device subcutaneously. In the case of subcutaneously implanted chemical glucose sensors, several major drawbacks are evident. First, the life-times of the devices are very limited, so that most of the current devices must be replaced within a few days. Secondly, the enzymatically impregnated membrane experience cell growth over them and deposition on extra-cellular secretions which drastically diminish the effectiveness of the device.

SUMMARY OF THE INVENTION

Because of the foregoing shortcomings of the prior art, there remains a substantial need for a device which is highly robust, i.e., one which yields highly repeatable measurements in an environment plagued by avoidable disturbances and non-linearities, is non-invasive, yields direct concentration measurements, and is continuous or near continuous in measuring concentrations of glucose, for the treatment of diabetes mellitus, and/or other biological substances. It is also desirable to provide an implantable device for providing an accurate measurement of glucose or other biological substances, whose measurement data can be interfaced to an infusion pump for automatic delivery of insulin or prescription drugs for treatment of other diseases.

Since biological systems can experience various physiological perturbations as a function of time and from one individual to another, it is desirable to provide an instrument that employs a highly robust "constant-baseline" comparative model that can be used for directly measuring concentrations of biological substances that are to be monitored. Of particular importance is the use of a constant-baseline comparative model that is robust with respect to molecular interactions of other biological analytes with the substance to be measured, for example glucose, when these interfering biological analytes are present in varying amounts and non-linearities (including those due to intermolecular interactions).

Descriptions of the utility of using an artificial neural network for robust discrimination of concentrations of biological substances when nonlinear data must be processed can be found in publications by F. M. Ham, et al. entitled "Glucose Sensing Using Infrared Absorption Spectroscopy and a Hybrid Artificial Neural Network," published in the proceedings of the 13th Annual International Conference IEEE Engineering in Medicine and Biology Society, Oct. 31–Nov. 3, 1991, Orlando, Fla., pp 1574–1576, "Improved Detection of Biological Substances Using a Hybrid Neural Network and Infrared Absorption Spectroscopy", published in the proceedings of the International Joint Conference on Neural Networks, Seattle, Wash., Jul. 8–12, 1991, and "Neural Network Based Real-Time Detection of Glucose Using a Non-Chemical Optical Sensor Approach," 12th Annual International Conference IEEE Engineering in Medicine and Biology Society, Nov. 1–4, 1990, Philadelphia, Pa., pp 480–482. Also, a paper by J. R. Long, et al, entitled "Spectroscopic Calibration and Quantitation Using Artificial Neural Networks", Analytical Chemistry, Vol. 62, No. 17, Sep. 1, 1990, pp 1791–1797, states that a neural network would be better for spectroscopic calibration than chemometrics for nonlinear phenomena.

It is also desirable to provide a constant-baseline comparative model that is capable of identifying outlier samples, and either reject the data as determined by the model as an anomaly, or yield a system response that indicates possible inclusion of this sample in the comparative model. In the latter case, the sample may have been a condition not previously considered in the model calibration process, which is associated with a physiological condition consistent with normal metabolic conditions.

Pursuant to the present invention, these needs are satisfied by a new and improved apparatus and method for determining concentrations of substances from biological samples, which uses Raman scattered light for analyzing biological fluids and/or tissues that have concentrations of various substances of interest, which can produce a variability of Raman scattered light intensities related to the concentrations of the substances. Substance concentration of a biological analyte or analytes is determined by comparing the Raman scattering intensity characteristics of the sample with a comparative model, in particular, an artificial neural network discriminator (ANND) that can be trained with a plurality of Raman spectral characteristics from biological fluids or tissue possessing known Raman scattered light intensities versus wavelength characteristics at known concentrations. A preferred implementation of the ANND employs fuzzy adaptive resonance theory-mapping (ART-MAP), which has excellent noise rejection capabilities and can readily handle nonlinear phenomena.

In a conference paper by F. M. Ham and S. W. Han, entitled: "Quantitative Study of the QRS Complex Using Fuzzy ARTMAP and the MIT/BIH Arrhythmia Database," published in the Proceedings of the WCNN-1993 International Neural Network Society Annual Meeting, Jul. 11–15, 1993, Portland, Oreg., Vol. II, pgs. 207–211, the authors describe the utility of fuzzy ARTMAP as a highly reliable discriminator to classify cardiac arrhythmias.

The ANND is trained with data that takes into account the following conditions: (1) overlapping spectra of non-interacting biological analytes of varying amounts with the spectrum of the biological substance of interest; (2) spectra associated with molecular interactions of certain biological substances of varying amounts with that of the biological analyte whose concentrations is to be monitored; (3) interactive spectra due to matrix effects, i.e., interactive spectra consisting of the biological analyte for which its concentration is desired and those materials used in the instrument that come into contact with body fluids or tissue to be analyzed; (4) noise and non-linearities associated with the spectroscopic instrument; (5) disturbances due to use of the instrument (e.g., positioning of a finger in the instrument); and (6) non-linearities due to the optical properties of skin and/or tissue. The training data inputs to the ANND contain multiple component intensities consisting of spectral bands around several selected characteristic wavelengths for glucose.

The present invention is also able to determine characteristics of biological substances for which outlier samples must be identified. The identification and removal of outlier samples from the calibration set (i.e. comparative model used for prediction) is extremely important to ensure a highly robust (reliable) discrimination process that predicts concentrations of biological substances. An outlier category of importance is not necessarily one of anomalies associated with instrumentation, positioning of a finger in the instrument, etc., but could result from insufficient calibration of the comparative model due to, for example, molecular interactions that have not previously been accounted for during the model calibration (i.e. training of the artificial neural network).

Robustness of the ANND with respect to outliers is undoubtedly one of the most important features of the discriminator. Repeated no decision detections at one extreme will never yield a result, which basically renders the methodology useless. At the other extreme, which possibly could involve false detections of concentrations of monitored substances, would be a worse situation because insulin replacement adjustments could be based on these readings.

As described above, outliers associated with incomplete calibration need to be included in the comparative model for fine "tuning" to increase accuracy and precision. Removal of this outlier data, as opposed to utilizing it for model "tuning", would actually degrade the instrument's accuracy and precision. Outlier data that is associated with instrumentation anomalies, etc. must be discarded and not utilized for model "tuning".

With this type of comparative model, artificial neural network discriminator (ANND), various levels of instrumentation noise, and other anomalies, can be used to train the ANND. These anomalies act to corrupt the spectroscopic data that the ANND must utilize to predict concentrations of certain substances of interest to be monitored, e.g. glucose. Therefore, the ANND is "trained" to recognize the data obscured by "noise" and thus, can associate concentrations of the substance to the noisy input data. This type of calibration (training) ensures ANND robustness, and thus, predicts concentrations reliably in the presence of outliers.

An outlier sample is a sample that does not exhibit characteristics consistent with the comparative model, i.e., the ANND comparative model, with which the sample data is compared for determining characteristics associated with the biological substance of interest. Outliers can be defined according to three classes: (1) outlier samples associated with instrumentation anomalies and other disturbances associated with the use of the instrument, but which have been accounted for in the training process of the ANND, and thus can be identified and accommodated by the instrument; (2) outlier samples associated with a physiological condition not previously considered in the model calibration process, i.e., training the ANND, but should be included in the comparative model; and (3) outlier samples that cannot be distinguished as belonging to either the first or second type of outlier samples previously explained, and should be discarded. For the second group of outlier samples, the ANND screens all sample data and, if this type of outlier sample is identified, the appropriate training steps are carried out to include this information in the comparative model. This process effectively 'tunes' the comparative model to enhance its robustness.

In accordance with an embodiment of the invention, the output beam from a near infrared, monochromatic light source, such as a laser diode which radiates a single spectral line (monochromatic) in the near infrared (NIR). The laser output is divided into two beams with a polarizing beam splitter. One portion of the split light beam is used to irradiate a sample that contains biological fluids being analyzed, in particular a finger, earlobe, or in vivo body fluids. Scattered light is collected from the sample using a set of mirrors and a focusing lens. Raleigh scattered light is removed by an optical filter and the remaining Raman scattered light is dispersed into various wavelengths by a diffraction grating. The dispersed Raman-scattered light from the irradiated sample impinges on the surface of a charge-coupled-device (CCD) array, which is divided into two portions by an optical shield. The use of Raman scattering makes it possible to 'tune' the monochromatic source wavelength, such that the Raman scattered energy will fall within the maximum responsivity of the CCD array.

The second portion of the split beam impinges on another diffraction grating, the output of which impinges on the second portion of the divided CCD array surface. Clocked outputs of the CCD array device are converted to digital signals using two synchronized analog-to-digital (A-D) converters. Rayleigh scattered light associated with the wavelength of the laser diode emitter is removed to avoid interference with the data to be analyzed. The two sets of electrical signals output from the CCD are transmitted to a digital signal processor, which is operative to take the ratio of the two signals in order to remove any intensity variations of the laser diode light source.

Concentration characteristics of biological analytes in body fluids in the sample are determined by processing the ratioed spectrophotometric data in an artificial neural network discriminator (ANND), which has been trained off-line with a plurality of Raman spectral characteristics of the substance of interest and known biological analytes that have interactions with the substance of interest. In particular, multiple NIR wavelengths associated with the Raman scattered light are analyzed by the trained ANND to determine concentrations of the substance of interest. Spectral intensity variations of the substance of interest are related to concentrations changes of the substance by way of the trained ANND. As noted above, in addition to this training procedure, training of the ANND is carried out with the same training data corrupted with noise indicative of instrumentation anomalies and other disturbances associated the use of the instrument. With the use of the ANND as an associative comparative model for classifying concentrations of the substance of interest, non-linearities arising from the spectroscopic instrumentation, anomalies associated with the use of the instrument, interactions with other molecules, and other interfering processes can be taken into account.

DETAILED DESCRIPTION

Figure 1:
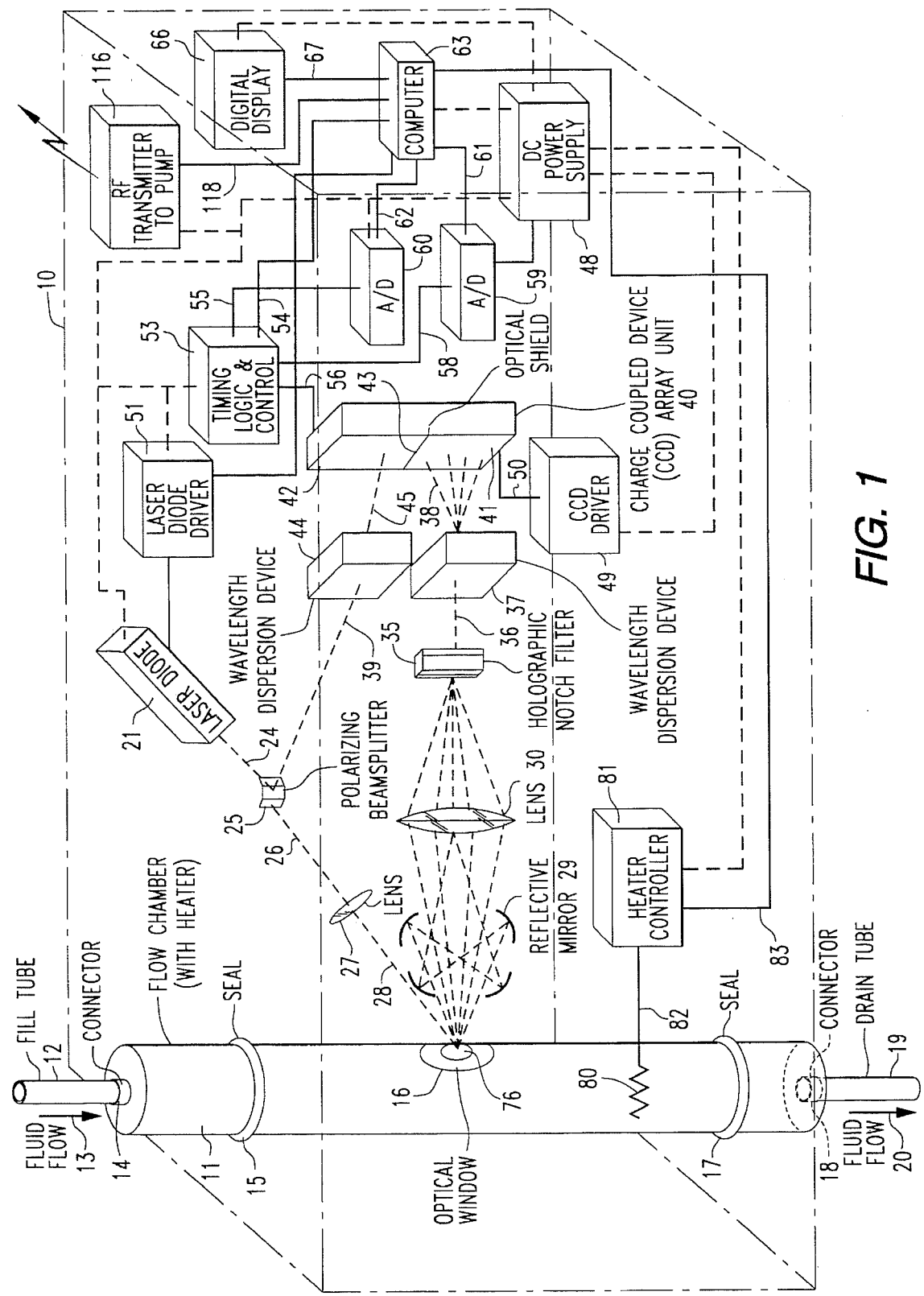
FIG. 1 is a diagrammatic perspective view of a first embodiment of the invention for monitoring in vitro biological fluids using near-infrared Raman spectroscopy.

Before describing in detail the particular improved apparatus and method for non-invasive determining the concentrations of a biological substance, such as glucose, by processing electro-optic signals obtained by Raman scattering by means of an artificial neural network discriminator, it should be observed that the present invention resides primarily in a novel structural combination of conventional signal processing and optical circuits and components and not in the particular detailed configurations thereof. Accordingly, the structure, control and arrangement of these conventional circuits and components have been illustrated in the drawings by readily understandable block diagrams which show only those specific details that are pertinent to the present invention, so as not to obscure the disclosure with structural details which will be readily apparent to those skilled in the art having the benefit of the description herein. Thus, the block diagram illustrations of the Figures do not necessarily represent the mechanical structural arrangement of the exemplary system, but are primarily intended to illustrate the major structural components of the system in a convenient functional grouping, whereby the present invention may be more readily understood.

FIG. 1 diagrammatically illustrates a first embodiment of the invention for monitoring in vitro biological fluids using near-infrared Raman spectroscopy, which may be employed for comparative model calibration. In the illustrated monitoring apparatus, the biological fluid of interest is supplied to a generally cylindrically shaped flow chamber 11 by way of an input or fill tube 12. Flow chamber 11 is retained in a housing 10, which contains the various components of the monitoring apparatus to be described. Respective seals 15 and 17 ensure a light-tight fit of flow chamber with housing 10. The direction of fluid flow is denoted by arrow 13. Fill tube 12 is joined to flow chamber 11 by way of a connector 14. The biological fluid is removed from flow chamber 11 by way of an output or drain tube 19. The direction of fluid flow from chamber through drain tube 19 is denoted by arrow 20.

Drain tube 19 is joined to flow chamber 11 by way of a connector 18. Fluid flow chamber 11 has an observation window 16 that allows the contents of the chamber to be irradiated by a light beam emitted by a monochromatic light source for the purpose of causing Raman scattering, as will be described.

More particularly, a monochromatic light source 21 (for example an SDL-5000 series laser diode, manufactured by SDL, Inc.), emits an output beam 24 that has a relatively safe (for human tissue use) low peak power on the order of 100 mW. As a non-limitative example, the wavelength of monochromatic laser diode source 21 may be a near infrared (NIR) light beam on the order of 780 nm. The choice of NIR source 22 is based upon a tradeoff study involving a set of detailed requirements for the entire system, such as: the preferred use of only "off-the-shelf" and solid state components; the use of spectroscopic techniques (Raman spectroscopy) to directly measure glucose concentration; the use of a near-infrared emitter to reduce fluorescence interference; the monochromatic near-infrared emitter (laser diode) emission frequency must be at a wavelength that maximizes Raman scattered light intensities for glucose, minimizes welter absorption, and penetration of the skin sufficiently, but safely, to directly measure blood glucose; the approach must be independent of skin pigmentation; the intensity of the near-infrared emitter must be high enough to ensure measurable levels of scattered light; and, as described in the text "Practical Laser Safety," by D. Winburn, Marcel Dekker, Inc., N.Y., pg 28, 1985, the optical power density must be an order of magnitude below the skin threshold of 4 $W/cm^2$.

A laser diode is callable of emitting a single spectral line, since the spectral linewidth is very narrow, for example, 0.001 nm is the linewidth of SDL-5400 series devices. Given the wavelength separation of the characteristic frequencies of D-glucose, and the fact that the intensity of scattered light increases with the frequency of the source, a monochromatic source having a wavelength of 780 nm turns out to be a preferred compromise for laser diode 21 considering the above tradeoffs.

The output NIR beam emitted by laser diode 21 is directed upon a polarizing beam-splitter 25, which decomposes laser output beam 24 into two beams, shown respectively being projected along paths 26 and 39. A first of the split beams, travelling along path 26, contains at least 96% of the 100 mWs of power provided by laser diode 21, and provides near-infrared energy which irradiates the medium (here fluid flow chamber 11) containing the fluid of interest. As will be described below with reference to FIGS. 5–9, in practical embodiments of non-invasive analysis of human glucose levels, beam 26 is directed onto tissue or vascular structure (e.g. a patient's finger) containing blood.

The beam 26 is focussed by a downstream lens 27 along path 28 and onto a concentrated portion 76 of an optical irradiation region or window 16 of the medium of interest (flow chamber 11 in FIG. 1). As the beam irradiates the sample, its electromagnetic energy interacts with the molecules within the biological fluid in the flow chamber and induces scattering of a portion of the electromagnetic energy in the beam. The scattered light consists of Stokes scattering (which is termed Raman scattered light) and Rayleigh scattering. Rayleigh scattered light has a wavelength which is the same as the wavelength of the source—laser diode 21. Raman scattered light, on the other hand, consists in general of a plurality of wavelength components, shifted with respect to the wavelength $\lambda_0$ of the irradiating source, and associated with the substance of interest in the sample. As will be described, these additional wavelengths of the Raman scattering are processed to determine the constituency of the sample.

Light scattered by the irradiated sample 11 is collected by way of a focussing optics arrangement containing a set of (four) reflective mirrors 29, and a lens 30 that focuses take scattered light, consisting of multiple wavelengths (Raman shifted wavelengths and Rayleigh or source wavelength) onto downstream optical components, for preliminary filtering and spatial dispersion. The viewing single at which the scattered light receiving optics is situated is preferably fixed in order to obtain repeatable results. The focussing optics arrangement preferably provides a beam size that leads to a power density which is an order of magnitude below 4 W/cm2. As shown in Table 1, referenced below, using a 780 nm NIR source for laser diode 21 results in a range of Raman wavelengths from 805.5 nm to 880.2 nm, corresponding to the eight highest intensity fundamental wavelengths of glucose (6.9 m to 25 m). These wavelengths are well within the responsivity of a downstream charge-coupled-device (CCD) array upon which the scattered light is directed, as will be described.

The focussed beam is directed onto a holographic notch filter 35, whose notch wavelength is very narrow and centered at the source wavelength $\lambda_0$=780 nm. Notch filter 35 is operative to remove the Rayleigh component of the light scattered from the irradiated medium, since the Rayleigh component has an intensity many orders of magnitude larger than the scattered light associated with Raman wavelengths from the collected and focussed scattered light energy from the irradiated sample.

The filtered light beam 36 emerging from notch filter 35 impinges on a wavelength dispersion device 37 (e.g. a diffraction grating having a suitable ruling spacing), so that the Raman wavelengths are spatially separated from one another along separate optical paths. The dispersed Raman scattered light components 38 impinge upon a first portion 41 of a CCD array unit 40, which captures the entire spectral content of the Raman scattered light that is to be monitored.

CCD array unit 40 preferably contains an ultra-low light CCD array, which has two distinct advantages over photodiodes. First of all, at least 10 dB improvement in measurement sensitivity can be achieved; also, advantage can be taken of the inherent integration characteristics of the CCD array to reduce noise. However, long integration times are avoided to reduce the effects of thermal gradients on the CCD array. If the integration times are excessive, thermal gradients can cause inaccurate intensity measurements. CCD array unit 40 is preferably an integrated unit containing amplification circuitry that adjusts the amplitudes of intensity variational data to a level that is suitable for downstream processing, e.g., A-D conversion. CCD array unit 40 may be thermoelectrically cooled, which results in low dark current, thereby allowing for long integration periods; the detector can be read once, thus minimizing noise that may accumulate over multiple readings.

The CCD array of unit 40 is optically partitioned by a light shield 43, so that a second other portion 42 of the CCD array may be used to monitor the fundamental NIR wavelength of laser diode source 21 directed along path 39 by polarizing beam splitter 25. Like the scattered light focussed by lens 30, the relatively small portion (approximately 4% of the 100 mWs of power provided by the laser diode 21), of the original beam 24 is diffracted by a wavelength dispersion device 44 along path 45 onto the second portion 42 of the partitioned CCD array, so that the array may monitor the wavelength of laser diode light source 21. Continuously monitoring the output of laser diode 21 in this manner enables downstream processing components to track any laser mode hops that occur as the temperature of the laser diode changes. Tracking irradiation source mode hops is necessary, since changes in source wavelength results in a change of the Raman wavelengths scattered from the sample. As long as the wavelength shift of the source can be accounted for, compensation can be provided in downstream signal processing to adjust the Raman scattered data.

CCD array unit 40 is driven, via link 50, by an associated CCD driver unit 49, which, like the other components of the apparatus, is powered by an attendant power supply 48, as shown. The scanned outputs from the first and second portions 41 and 42 of the CCD array are coupled over CCD output link 56 to a set of timing logic and control circuits 53, which clock signals representative of Raman wavelength component intensity values from the first portion 41 of the CCD array, and the laser diode monitoring signal from the second array portion 42, over links 58 and 54 to respective analog-to-digital (A-D) converters 59 and 60. Digitized data from A-D converters 59 and 60 are coupled over links 61 and 62 to a system processor 63 for analysis. Processor 63 may comprise a 68000 series-based microprocessor manufactured by Motorola Incorporated. A non-limitative example of a control and signal processing mechanism that may be employed by processor 63 in the course of the operation of the invention is shown in detail in the FIGS. 11, 12 and 13, to be described.

The data received by processor 63 is initially pre-processed by performing noise-reduction signal processing, and then ratio of the data representative of the intensities of Raman-scattered wavelengths to the data representative of the intensity of the NIR laser diode source is derived for each wavelength of the Raman-scattered components. If mode hop compensation for laser diode 21, referenced above, is necessary, such compensation is performed prior to deriving the intensity ratios for the respective Raman scattered wavelengths. The purpose of the ratio step is to normalize the data relative to the laser source and thereby eliminate the effect of any intensity variations of the laser diode.

In addition, because the intensities of vibrational Raman scattering are temperature dependent, as is the case with infrared absorption spectroscopy, the localized temperature at the site at which the source energy impinges, flow chamber 11 in the embodiment of FIG. 1, is controlled to standardize the results relative to temperature. For this purpose, a heating element, shown schematically at 80, may be coupled with (e.g. wrapped around or embedded in) the sidewalls of the flow chamber 11 and a heater control unit 81 coupled to the heating element coupled via a control link 82. Heater control unit 81 is controlled by system processor 63 via link 83. A thermo-sensor, not shown, may be coupled with flow chamber 11 in the vicinity of irradiation window 16, the output of the thermo-sensor being coupled to processor 63, so that the processor may track and adjust the chamber temperature, as necessary, via heater control unit 81 and heating element 80. In a transient case the temperature is monitored continuously and compensated for changes from a target value.

Also, as part of the noise-reduction signal processing carried out during pre-processing of the data to be analyzed to determine the concentration of the biological analyte of interest (e.g. glucose), an intensity versus wavelength selection process may be performed. Multiple scans of the sample may be carried out and successive sets of outputs averaged, so as to further reduce any effects of system noise.

Additionally shown in FIG. 1 is an RF transmitter unit 116, which is operative to transmit a control signal to an attendant patient utility device, such as an insulin metering pump, that is invasively connected with the patient, for controllably adjusting the supply of insulin to the monitored patient on the basis of monitored glucose concentration. For this purpose, processor 63 couples a control signal via link 118 to RF transmitter 116 which signals an associated receiver to which the remote insulin metering unit is coupled.

As described briefly above, the data processing mechanism employed by processor 63 is operative to determine the concentration of the biological analyte or analytes within the sample being irradiated by comparing Raman scattering intensity data with a comparative model, specifically, an artificial neural network discriminator (ANND), to be described, that has been trained off-line with a plurality of Raman spectral characteristics of the substance of interest and known biological analytes that have interactions with the substance of interest. Multiple NIR wavelengths associated with the Raman scattered light are analyzed by the trained ANND to determine concentrations of the substance of interest. Spectral intensity variations of the substance of interest are related to concentrations changes of the substance by way of the trained ANND.

Since Raman scattering data provide detailed information on vibrations of molecules, the data is indicative of structural information about the molecules. This information is used to identify and quantify concentrations of substances in the medium being analyzed, so as to produce a "fingerprint" of the substance. This phenomenon occurs due to the fact that light scattered off an irradiated molecule results in an energy exchange in discrete units that corresponds to vibrational energies of that molecule.

More particularly, when light of energy $E_o = h\nu_o$ (where $h = 6.62 \times 10^{-27}$ is Planck's constant and $\nu_o$ is the frequency of the monochromatic light source) impinges on a molecule and light, which is scattered from the molecule, has the same energy $E_o$ (or the same frequency $\nu_o$), the resultant scattering is termed Rayleigh scattering. However, depending on the molecular structure of the substance in the sample, interactions between the irradiating light beam and the molecule will cause the molecule to be elevated to a different energy level (Stokes scattering) with a concomitant loss of energy in the scattered light. This phenomenon is termed Raman scattering, and the wavelengths associated with the shifted energy levels constitute the molecular "fingerprint" of the substance. Even though the frequency shifts $(\nu_o - \nu_i)$ are exceedingly small, the wavelength shifts can be very large, since $\lambda = c/\nu$ (where c is the speed of light).

As described in the text "Laser Raman Spectroscopy," by M. Tobin, R. E. Krieger Publ. Co., Malabar Fla. 1982, concentrations of glucose can be related to relative Raman spectral intensities by way of a relationship which is given as $$(\Delta I) BAR = \rho \sigma (\Delta X) \Delta I_o \tag{1}$$

where $(\Delta I)$ is the total scattered power, $\rho$ is number of molecules per cm$^3$, $\sigma$ is the total scattering cross section (cm$^2$), $\Delta X$ is the length (cm) of the illuminated volume, A is the cross-sectional area (cm$^2$) of the illuminated volume, and $I_o$ is the flux density of the incident monochromatic light beam (W/cm$^2$). Equation (1) corresponds to Beer's law for loss of energy of the incident beam due to Raman scattering into the particular Raman band being considered.

Therefore, Equation (1) can be rewritten as $$(\Delta I)BAR = \kappa I \Delta X \tag{2}$$

where $\kappa$ is the loss coefficient in $cm^{-1}$.

When a 780 nm monochromatic near-infrared light source (corresponding to the source wavelength of laser diode 21 in the presently described embodiment) is used to irradiate a pure sample of anhydrous D-glucose ($C_6H_{12}O_6$), the resultant scattered light will consist of both Raleigh and Raman scattering. Glucose has a rich Raman spectrum with eight fundamental wavelengths at $\Delta\lambda_i$ (for i=1,2, . . . 8) equal to 6.85, 7.44, 8.93, 9.31, 10.93, 11.89, 18.47, and 24.67 μm. These fundamental wavelengths constitute a change or shift in the wavelength ($\Delta\lambda_i$) relative to the wavelength $\lambda_o$ of the source energy ($E_o$), i.e., $\Delta v_i = v_0 - v_i = c/v_o - c/v_i$, or, in terms of wavenumber, $\Delta v'_i = v'_0 - v'_i = 1/v_o - 1/v_i$ (where v'=1/v cm−1 and $1/\Delta v'_i = \Delta v'_i$).

Therefore, the expression for the wavelength shift $\Delta\lambda_i$ can be written as:

$$1/\Delta\lambda_i = 1/\lambda_o - 1/\lambda_i \tag{3}$$

Solving for $\lambda_i$ from Equation (3) yields $$\lambda_i = \lambda_o \Delta\lambda_i / (\Delta\lambda_i - \lambda_o) \tag{4}$$

where $\Delta\lambda_i$ are the characteristic wavelengths having peak intensities which constitute the major portion of the molecular "fingerprint" of the particular molecule which is irradiated with monochromatic light of wavelength $\lambda_o$, and $\lambda_i$ (for i=1, 2, 3 . . . ) are the associated wavelengths of the Raman scattered light being detected. Since the values of $\Delta\lambda_i$s do not change for the anhydrous substance alone, and for a fixed monochromatic light source at a wavelength of $\lambda_o$, the $\lambda_i$ s will also be fixed and depend only upon the wavelength of the irradiating light source, as can be seen from equation (4).

Figure 2:
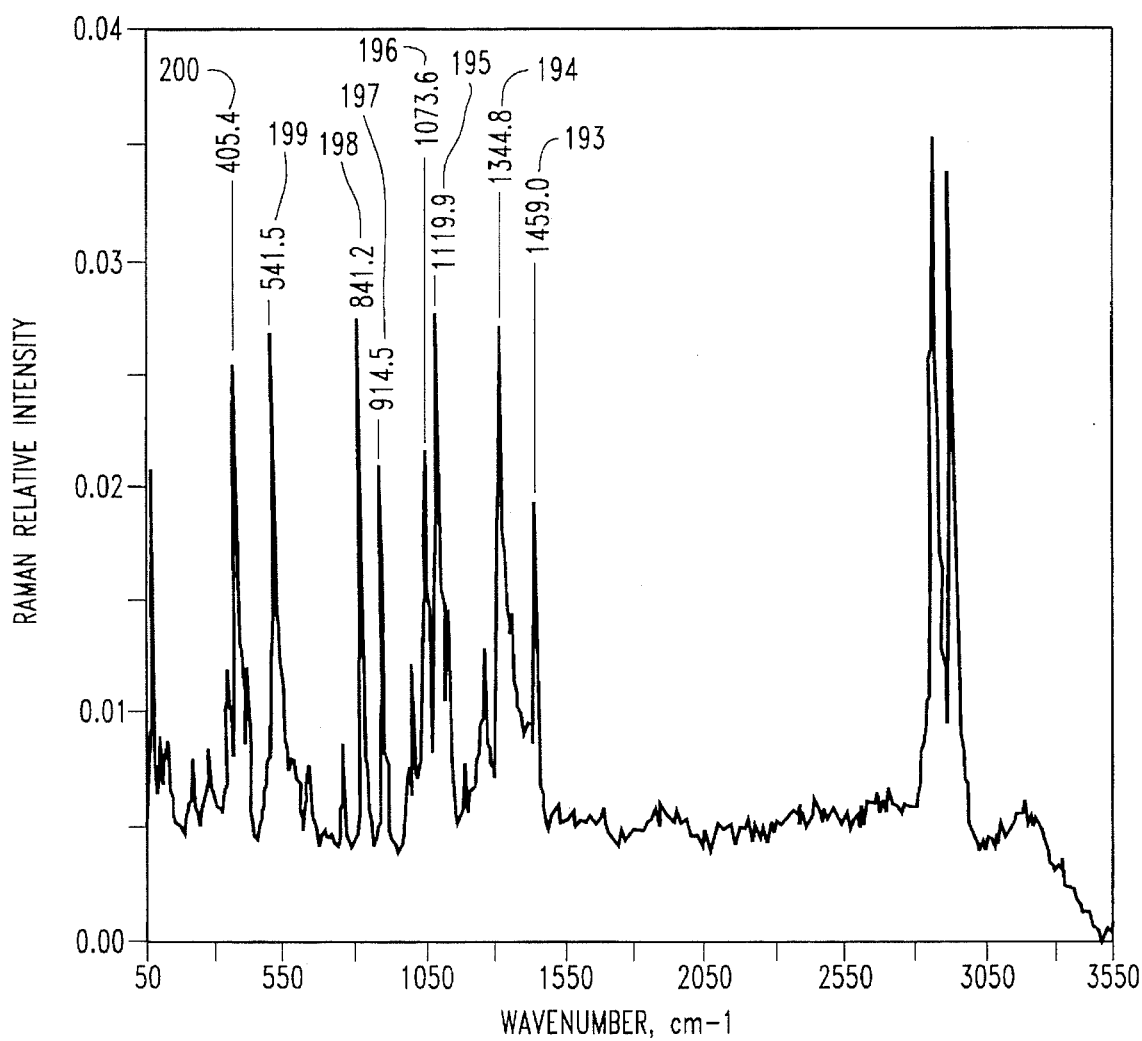
FIG. 2 shows the Raman spectrum of anhydrous D-glucose ($C_6H_{12}O_6$) specifically showing eight fundamental Raman wavelengths of glucose.

Table 1 below shows the resultant wavelengths of the Raman scattered light ($\lambda_i$s), that were calculated using Equation (4), for anhydrous D-glucose ($C_6H_{12}O_6$), using a 780 nm monochromatic light source, while FIG. 2 shows the Raman spectrum of anhydrous D-glucose ($C_6H_{12}O_6$) specifically showing eight fundamental Raman wavelengths of glucose.

TABLE 1

Raman Scattering Data for Anhydrous D-Glucose ($C_6H_{12}O_6$)
Source Wavelength: $\lambda_0$ = 780 nm

| $\Delta v_i'$, cm$^{-1}$ | $\Delta\lambda_i$, μm | $\lambda_i$, nm |
| --- | --- | --- |
| 1459.0 | 6.85 | 880.2 |
| 1344.8 | 7.44 | 871.4 |
| 1119.9 | 8.93 | 854.7 |
| 1073.6 | 9.31 | 851.3 |
| 914.5 | 10.93 | 839.9 |
| 841.2 | 11.89 | 834.8 |
| 541.5 | 18.47 | 814.4 |
| 405.4 | 24.67 | 805.5 |
|  |  | Avg. = 844 nm |

The Raman data ($\Delta v'_i$s) shown in Table 1 and the Raman spectral line data illustrated in FIG. 2 were derived using a Bruker FRA-106 FT-NIR Raman spectrophotometer, which employs a 1.064 μm pumped Nd:YAG laser light source set at 200 mW output power, a liquid nitrogen-cooled germanium detector, and 100 scans. The wavenumbers ($\Delta v'_i$s) were computer-selected values from the Bruker system.

ARTIFICIAL NEURAL NETWORK DISCRIMINATOR (ANND)

As described briefly above, a preferred embodiment of the comparative model for processing the preliminarily ratioed Raman-scattered data is an artificial neural network discriminator (ANND), that is trained with a plurality of spectral data from known biological fluid samples. The Raman spectrum of the scattered light will consist of a least a portion, if not all, of the above-listed contributors to the effective spectrum. The information that must be extracted in order to make a concentration decision based on comparisons with the ANND resides, or is effectively "buried" in the effective spectrum. Advantageously, however, the ANND possesses a robust discrimination capability that enables it to reliably extract this information and classify the proper concentration of the biological component of interest. Preferably, the AAND employs fuzzy ARTMAP (adaptive resonance theory-mapping), to be described, which has excellent noise rejection capabilities so that it is readily able to handle nonlinearities.

The ANND is trained with a training data set that is derived from one configuration of the instrument that is adapted only for the purpose of accumulating data for the training of the ANND. The training data set consists vectors v which are contained in a vector space V, with each vector containing 2 xp normalized elements. There are p components of the vector which are associated with Raman scattering intensities as a function of wavelengths, including n fundamental wavelengths of the biological component to be monitored (i.e., the biological analyte whose concentration is to be determined) and an m (m is an odd integer so as to include the fundamental wavelength) component spectral band about each of the n fundamental wavelengths, therefore p=nxm (where m<n). The vectors are actually of length 2 xp, since a complementary coding scheme is used for a fuzzy ARTMAP, i.e., for every one of the p components in v, its associated complementary value is also included, thus, the vectors v are of length 2 xp.

The training set vectors are derived from and include:

(1) spectra of noninteracting biological analytes of varying amounts that can overlap with that of the biological component spectrum alone;

(2) spectra associated with molecular interactions of certain biological components of varying amounts with that of the biological analyte whose concentrations are to be monitored (e.g., glucose);

(3) spectra associated with molecular interactions of prescribed prescription drugs or social drugs of varying amounts with that of the biological analyte whose concentrations are to be monitored;

(4) interactive spectra due to matrix effects, i.e., the interactive spectra consisting of the biological analyte whose concentration is desired and those materials used in the instrument that come into contact with body fluids or tissue to be analyzed;

(5) noise and nonlinearities associated with the spectroscopic instrument and otherwise possible nonlinearities;

(6) disturbances due to use of the instrument itself (e.g., positioning of a finger in the instrument); and (7) nonlinearities due to optical properties of skin and/or tissue.

FUZZY ARTMAP

As described in an article by Carpenter et al, entitled "Fuzzy ARTMAP: A Neural Network Architecture for Incremental Supervised Learning of Analog Multidimensional Maps", IEEE Transactions on Neural Networks, Vol. 3, No 5, pgs. 698–713, (1992), a Fuzzy ARTMAP is a clustering neural network that constructs as many categories (clusters) as needed to classify, for example, a range of concentrations by increasing the fuzzy ART vigilance parameter by the minimum amount needed to correct a predictive error. A fuzzy ARTMAP has excellent inherent noise rejection capabilities which is necessary for an instrument that must provide highly reliable responses for classification of concentrations of biological analytes, for example, in a sample.

Figure 3:
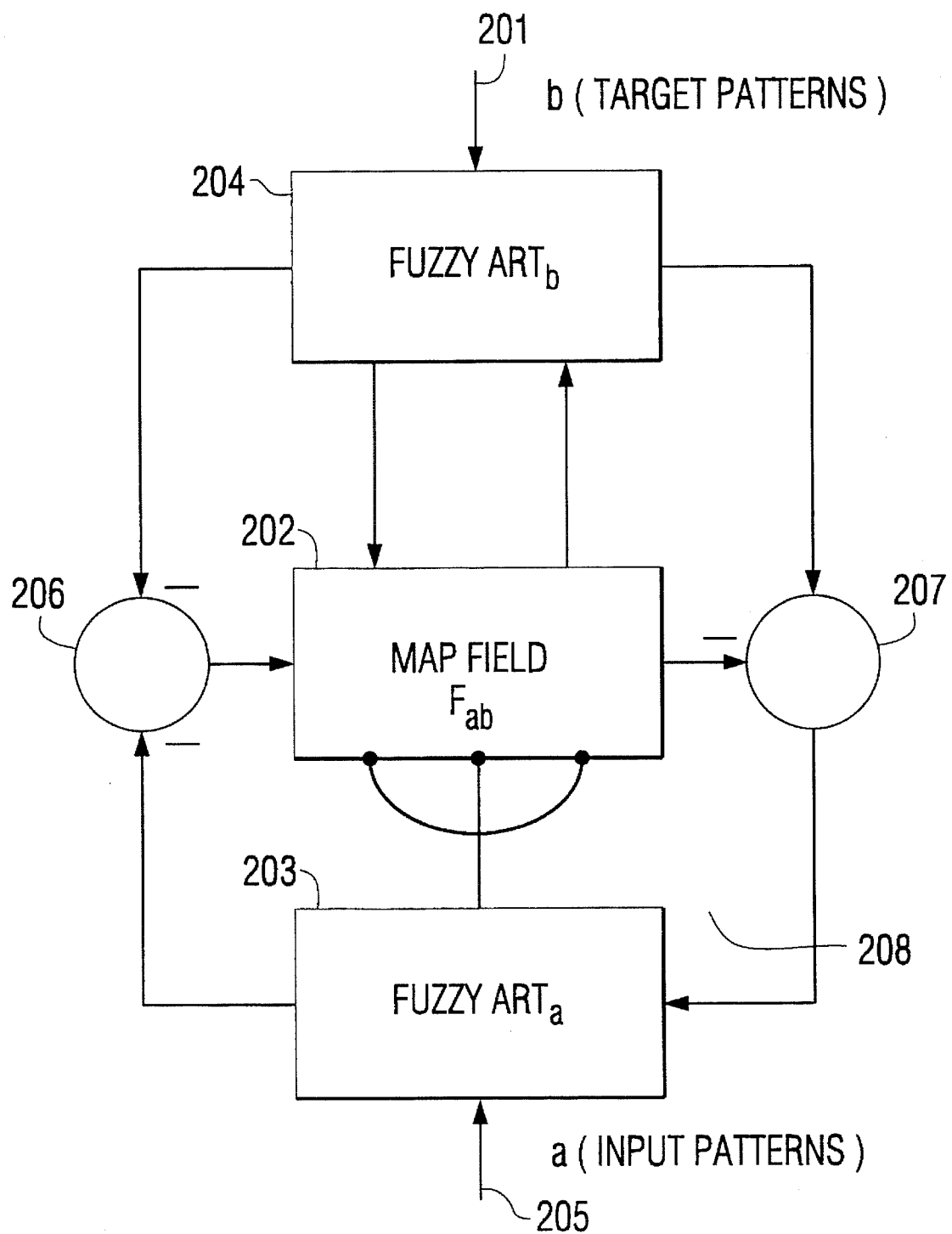
FIG. 3 diagrammatically illustrates the basic architecture of a fuzzy adaptive resonance theory-mapping artificial neural network.

Once the fuzzy ARTMAP is trained with enough exemplars to create a robust comparative model, i.e. an artificial neural network discriminator (ANND), it is capable of discriminating concentrations of biological components of interest contained in a sample. The basic architecture of a fuzzy ARTMAP is diagrammatically illustrated in FIG. 3 as incorporating two fuzzy ART modules, $ART_a$ 203 and $ART_b$ 204, are linked together via an inter-ART module, $F_{ab}$, that consists of the map field 202 and control nodes as a Map Field gain control 206 and a Map Field orienting subsystem 207. The map field 202 is used to form predictive associations between categories and to realize the match tracking rule, whereby the vigilance parameter of $ART_a$ 203, ρa, increases in response to a predictive mismatch at $ART_b$ 204. Match tracking path 208 reorganizes the category structure, so that the predictive error is not repeated on subsequent presentations of the input.

During the training period, the $ART_a$ 203 module receives a data stream {a} 205 of input patterns and $ART_b$ 204 receives a data stream {b} 201 of target patterns, where b is a corresponding target to a. If a vector a 205 is associated with a vector b 201, then any other input that activates the a's category node will predict the category of target pattern b. However, when a mismatch at the map field between the $ART_a$ category activated by an input a and the $ART_b$ category activated by the input b occurs, the net increases the $ART_a$ vigilance parameter, $ρ_a$, by the minimum amount needed to search for and, if necessary, create a new cluster (category). The new cluster is created to learn a new $ART_a$ category whose prediction matches the $ART_b$ category.

After training is completed, which means that the neural network predicts a correct corresponding target pattern for each of the training input patterns, the test input patterns are presented at $ART_a$ without the use of $ART_b$. The (–) signs of the architecture of FIG. 3 denote inhibitory paths, whereas the other paths are excitatory. There are a number training methods that can be used for the fuzzy ARTMAP network. As described in an article by F. Ham et al., entitled "Quantitative Study of the QRS Complex Using Fuzzy ARTMAP and the MIT/BIH Arrhythmia Database", Proceedings of the WCNN-93 Inter. Neural Network Soc. Annual Mtg. Portland, Oreg. Jul. 11–15, 1993, Vol. II, pp 207–211, the fast learning algorithm has proven to be sufficient for training this type of neural network. The parameters that must be selected for the training process are: learning rate, choice parameter, vigilance parameter for $ART_a$, vigilance parameter for $ART_b$, and the map field parameter.

Figure 4:
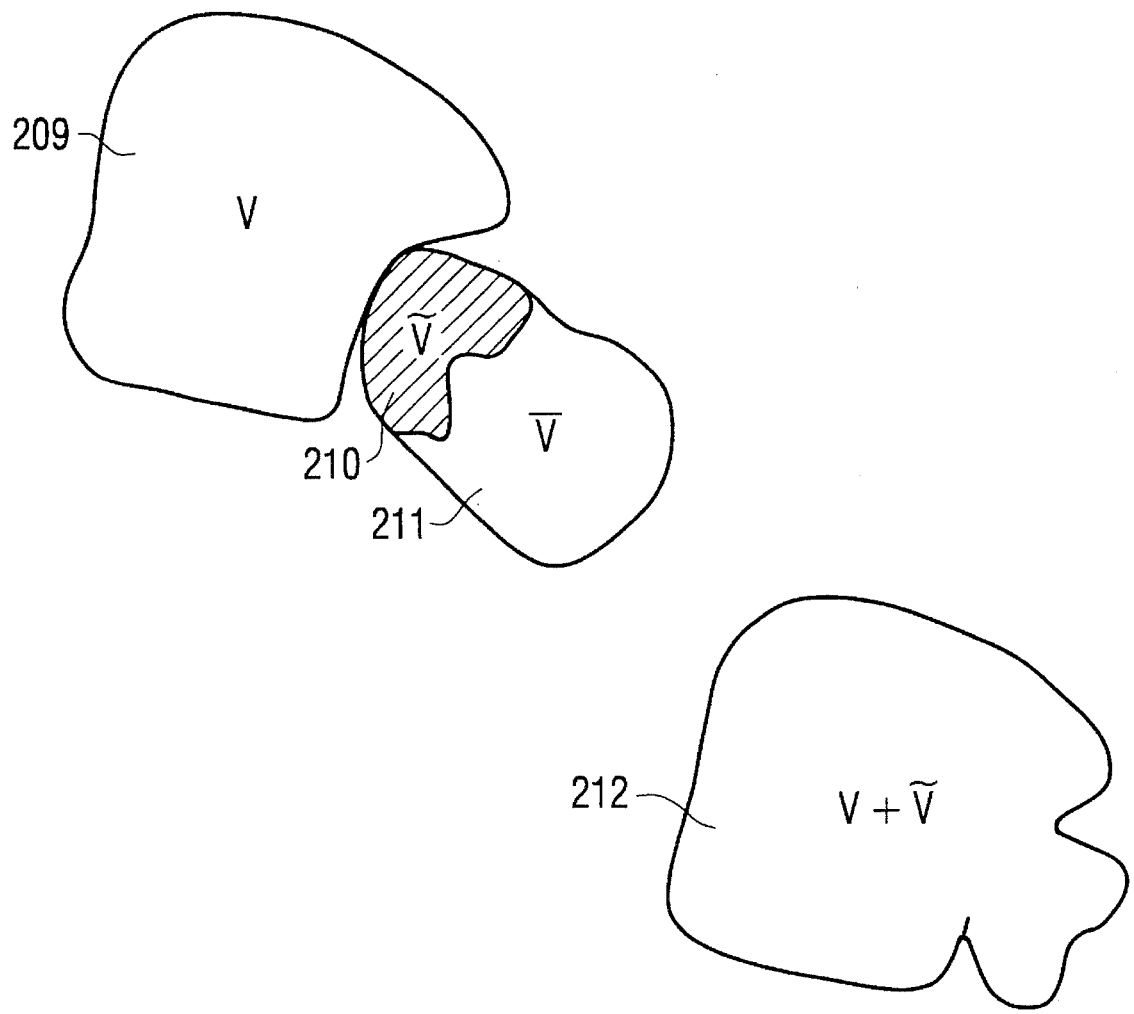
FIG. 4 diagrammatically illustrates training vector space diagrams for training an artificial neural network.

As explained previously, the ANND is trained with a training data set that is derived in accordance with a configuration of the instrument (such as that shown in FIG. 1) which is adapted only for the purpose of accumulating data for training the ANND. As shown in FIG. 4, each of the training vectors v resides in a vector space V 209, which constitutes the initial set of training vectors. These vectors are presented to the fuzzy ARTMAP ANND, together with their associated target vectors for supervised learning, using a defined voting strategy approach. The voting strategy approach defines a structured reordering of the training vector inputs to the ANND, which can reduce possible incorrect classification of data.

After the initial training of the ANND, further system testing procedures may reveal untrained data that must be included in the comparative ANND model. This set of untrained vectors, shown in the vector space 210, must eventually be included in the comparative model, such that the resultant ANND is as robust as possible. This data, together with the associated target vector data, can used to further train the ANND without any retraining necessary using any of the previous training vectors. The vector space is a subspace of the vector space 211, which also contains vectors associated with other outlier data that must not be included in the comparative model, but have either been accounted for during the initial training process of the ANND or can be identified as outlier samples by the ANND and appropriately discarded.

After inclusion of the vector subspace V 210 with the original training data included in the vector space V 209, the resultant vector space 212 of training vectors (V+V') will include a comprehensive set of training vectors. When the entire vector space has been used to train the ANND, the comparative model is effectively optimized. However, continuous exhaustive retraining of the ANND is not practical, therefore, the ANND is trained until its classification performance exceeds a predetermined threshold, so that the instrument can produce highly repeatable results and is thus near optimal and highly robust.

The intensity variation Raman-scattering data, which is a function of wavelength, i.e., the 2 xp length vectors v, are transmitted to the subsystem module contained within processor 63 that the ANND (which has been trained to meet a specified set of performance criteria). The 2 xp length vectors v are compared to the ANND comparative model whose output is a category (cluster) associated with either (1) a concentration value, (2) no decision—continue monitoring, (3) system learning—storing data—continue monitoring, (4) system learning—storing data—system error—restart, or (5) system learning—storing data system error—check unit. All of these five system responses provided by the ANND are coupled, as shown in FIG. 1, via data link 67 to a digital display 66 for presentation to the operator.

In addition to determining the concentration of target substances in an irradiated sample, the present invention is also able to determine characteristics of biological substances for which outlier samples must be identified. An outlier sample is a sample that does not exhibit characteristics consistent with the comparative model, i.e., the ANND comparative model, with which the sample data is compared for determining characteristics associated with the biological substance of interest.

Outliers can be defined according to three classes:

(1) outlier samples associated with instrumentation anomalies and other disturbances associated with the use of the instrument, but which have been accounted for in the training process of the ANND, and thus can be identified and accommodated by the instrument;

(2) outlier samples associated with a physiological condition not previously considered in the model calibration process, i.e., training the ANND, but should be included in the comparative model; and (3) outlier samples that cannot be distinguished as belonging to either the first or second type of outlier samples previously explained, and should be discarded.

For the second group of outlier samples, the ANND screens all sample data and, if this type of outlier sample is identified, the appropriate training steps are carried out to include this information in the comparative model. This process effectively 'tunes' the comparative model to enhance its robustness.

Figure 5:
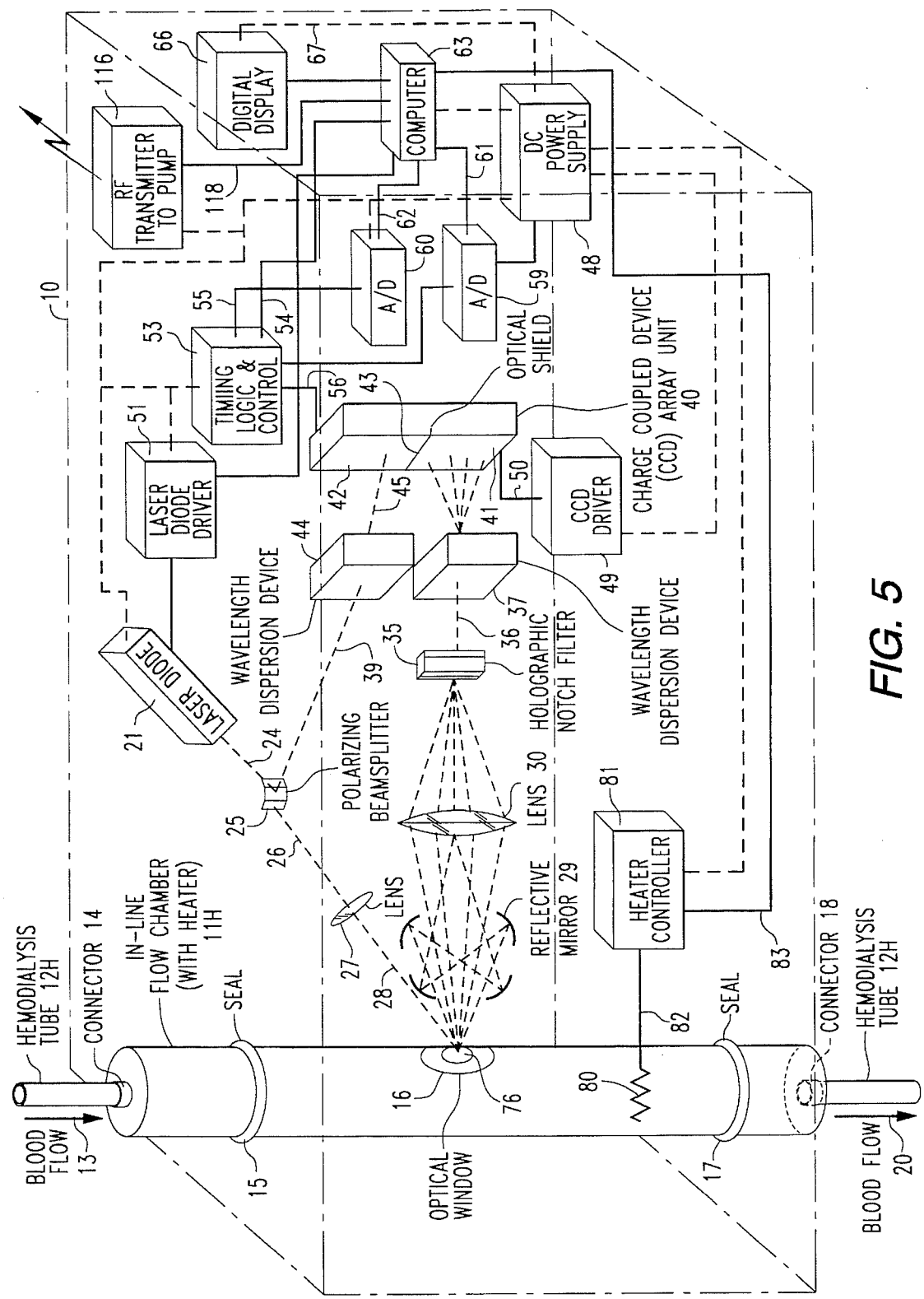
FIG. 5 is a schematic, perspective view of a modification of the embodiment of the invention of FIG. 1, which is adapted for use in monitoring blood components during hemodialysis.

FIG. 5 is a schematic, perspective view of a modification of the embodiment of the invention of Figure 1, which is adapted for use in monitoring blood components during hemodialysis in which the fluid flow chamber 11 corresponds to a hemodialysis tube, that has been secured in the instrument housing 10. Except for the fact that the input tube to in-line flow chamber 11H is a hemodialysis tube 12H, the components of the embodiment of the invention depicted in FIG. 5 are the same as those of FIG. 1, and will not be described in detail here.

Figure 6:
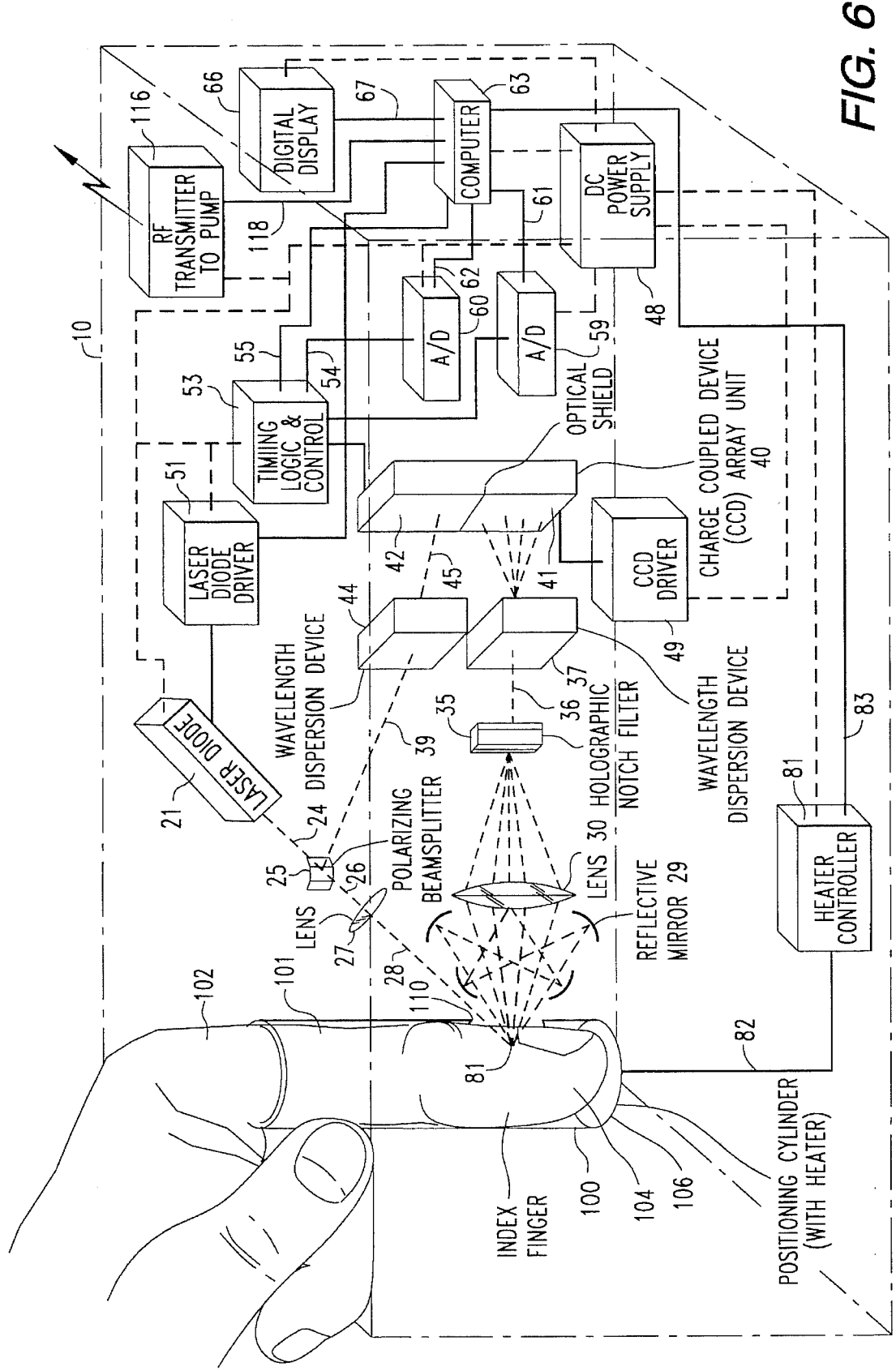
FIG. 6 shows a schematic, perspective view of a third embodiment of the invention, which is particularly adapted for non-invasive monitoring of blood components (in particular glucose) in the distal portion of a human (e.g. index) finger.

Referring now to FIG. 6, there is shown a schematic, perspective view of a third embodiment of the invention, which is particularly adapted for non-invasive monitoring of blood components (in particular glucose) in the distal portion of a human (e.g. index) finger. For this purpose, a receptacle 100, such as a generally cylindrically shaped tube, having an opening 101 that is sized to accommodate the insertion of a human index finger 102, is configured such that the distal end 104 of the finger may come to rest against an interior bottom or floor portion 106 of the tube. Tube 100 has an opening or window 110 which exposes a 111 portion of the skin surface of the patient's finger to incident optical beam 28, so that, as in the embodiment of FIG. 1, described above, the tissue of the finger may be irradiated by light beam 28 emitted by laser diode 21 and thereby produce Raman scattering. It should be noted that the invention is operative to irradiate the skin of the patient's finger regardless of the orientation of the finger in the tube.

Again, as in the embodiment of FIG. 5, for the most part, the components of the embodiment of the invention depicted in FIG. 6 are the same as those of FIG. 1. It may be noted, however, that the above described choice of monochromatic NIR light source 21 as having a wavelength on the order of 780 nm and having a relatively low peak power on the order of 100 mW is an important feature of the embodiment of FIG. 6, in that it maximizes Raman scattered light intensities for glucose, minimizes water absorption, and penetration of the skin sufficiently, but safely, to directly measure blood glucose. Although the optical power density of its output beam is an order of magnitude below the skin threshold of 4 W/cm$^2$, the intensity of the near-infrared laser diode 21 is sufficiently high to ensure measurable levels of scattered light.

As in the embodiment of FIG. 1, the Raman scattering data output by the scanning of CCD array unit 40 is digitized and processed by the ANND employed by processor 63. Also, like the embodiment of FIG. 5, the embodiment of FIG. 6 employs an RF transmitter unit 116, which is operative to transmit a control signal to an attendant patient utility device, such as an insulin metering pump, that is invasively connected with the patient, for controllably adjusting the supply of insulin to the monitored patient on the basis of monitored glucose concentration.

Figure 7:
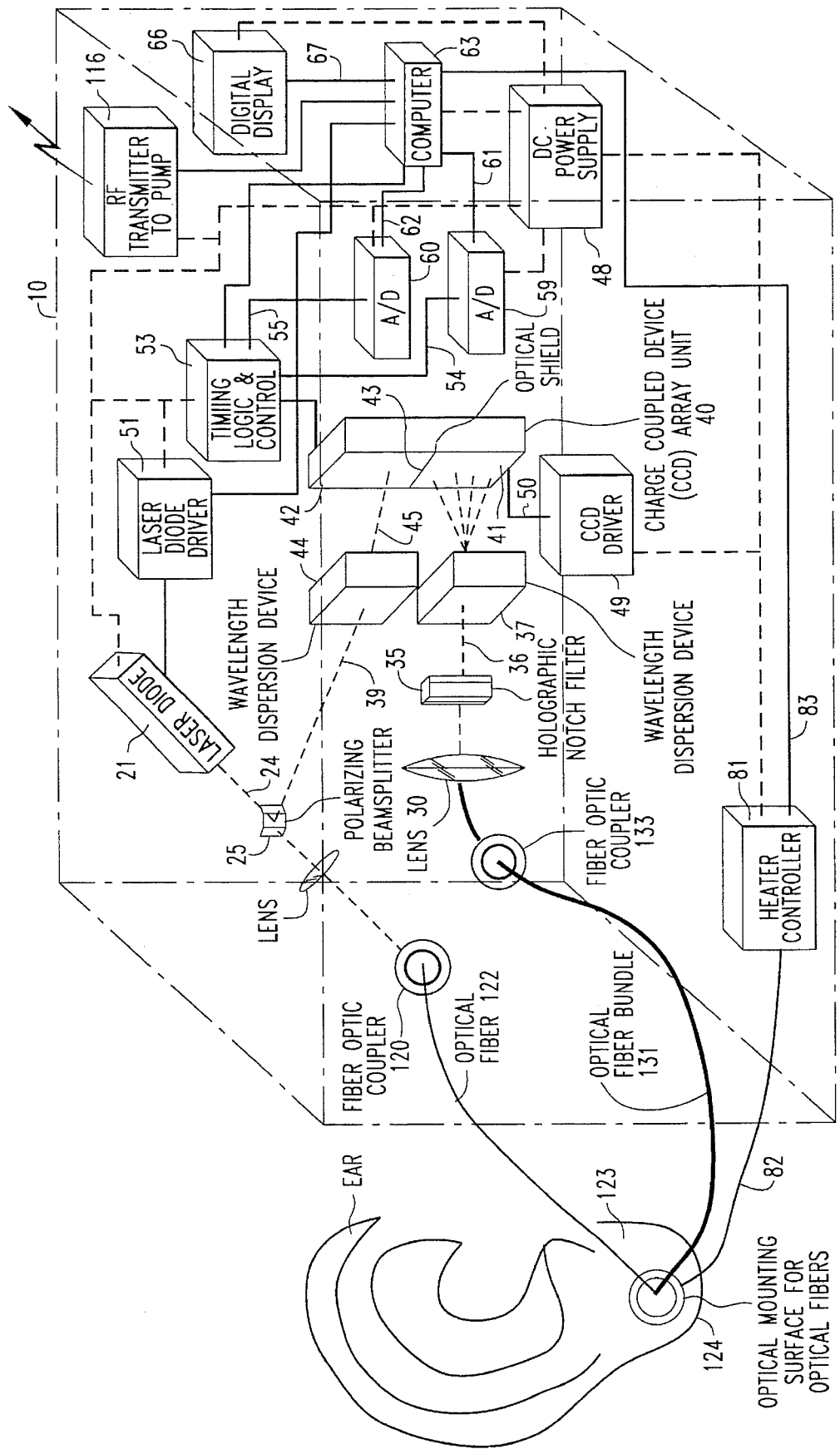
FIG. 7 is a schematic, perspective view of a further embodiment of the invention adapted for use with an optical fiber to direct near-infrared source energy to a connection element that may be worn by the patient, so that the patient may continuously monitor glucose concentrations.

FIG. 7 is a schematic, perspective view of a further embodiment of the invention adapted for use with an optical fiber to direct near-infrared source energy to a connection element that may be worn by the patient, so that the patient may continuously monitor glucose concentration. In the non-limitative example, illustrated in FIG. 7, the unit is adapted to be coupled to a readily accessible portion of human tissue, such as the patient's earlobe, by means of an optical fiber arrangement. Namely, rather than irradiate a window of a tube in which the substance to be analyzed has been placed, as in the embodiments of FIGS. 1, 5 and 6, the embodiment of FIG. 7 couples the irradiation beam travelling along path 28 to a fiber optical coupler 120, to which a section of optical fiber 122 is connected. The optical fiber 122 is coupled to the patient's earlobe 123 by means of a physical attachment element 124, which may include a coupling lens adjacent to the surface of the skin. Attachment element 124 is also coupled to receive one end of an optical fiber bundle 131, which receives the scattered light and couples the scattered light to an optical fiber coupler 133 contained in the instrument housing 10. The output of optical fiber coupler 133 is coupled to lens 30 which focusses the scattered light as in the embodiment of FIG. 1.

Figure 8:
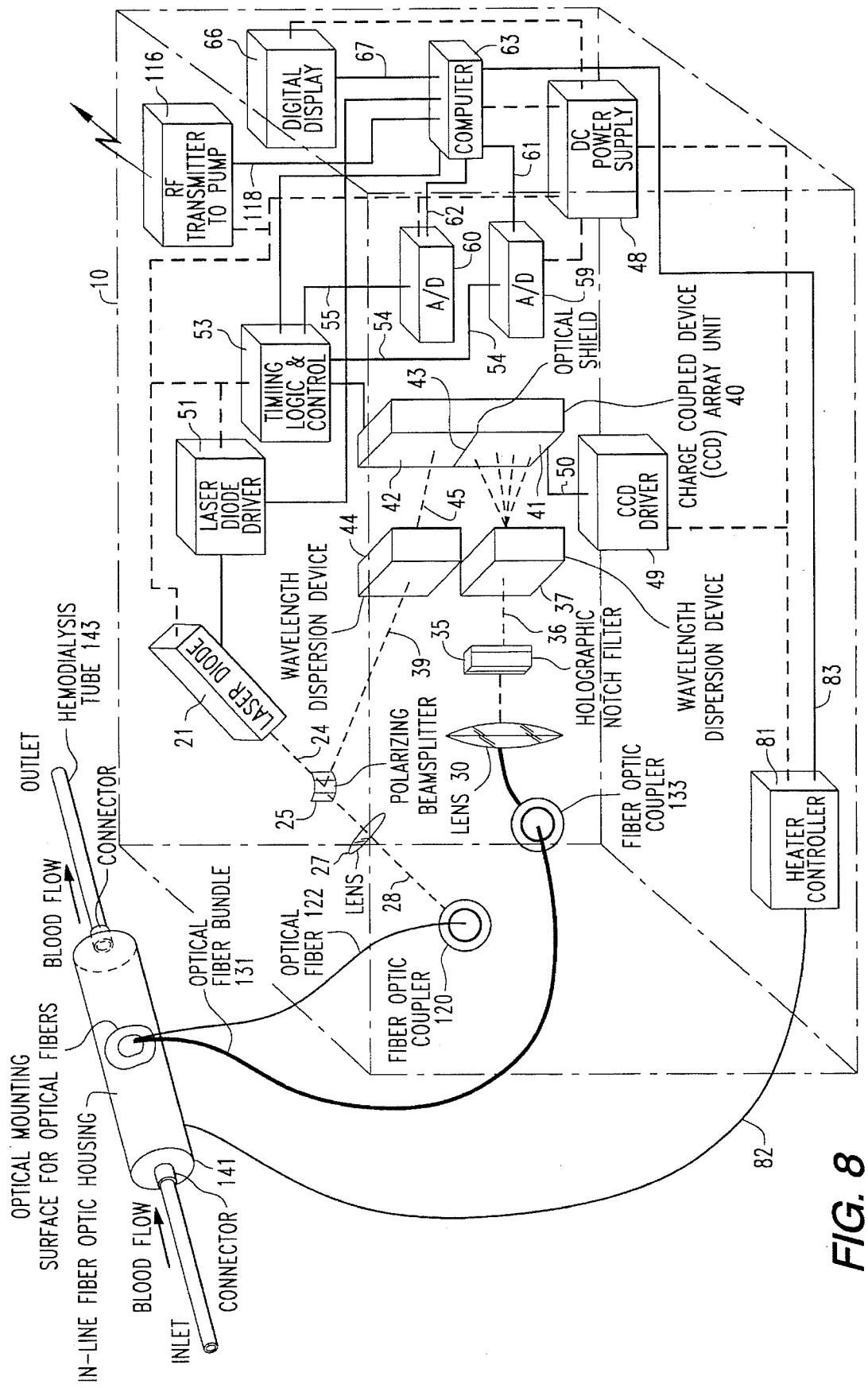
FIG. 8 is a schematic, perspective view of another embodiment of the invention adapted for use in monitoring blood components during hemodialysis using an optical fiber arrangement of the type described above with reference to the embodiment of FIG. 7.

FIG. 8 is a schematic, perspective view of another embodiment of the invention adapted for use in monitoring blood components during hemodialysis using an optical fiber arrangement of the type described above with reference to the embodiment of FIG. 7, to direct near-infrared source energy from laser diode 21 to an optical housing 141 that is connected to a hemodialysis tube 143. In the configuration of FIG. 8, the fiber mounting fixture 124 for the optical fiber arrangement (irradiating fiber 122 and scattering-receiving bundle 131) is mounted upon the outer surface of hemodialysis tube 143.

Figure 9:
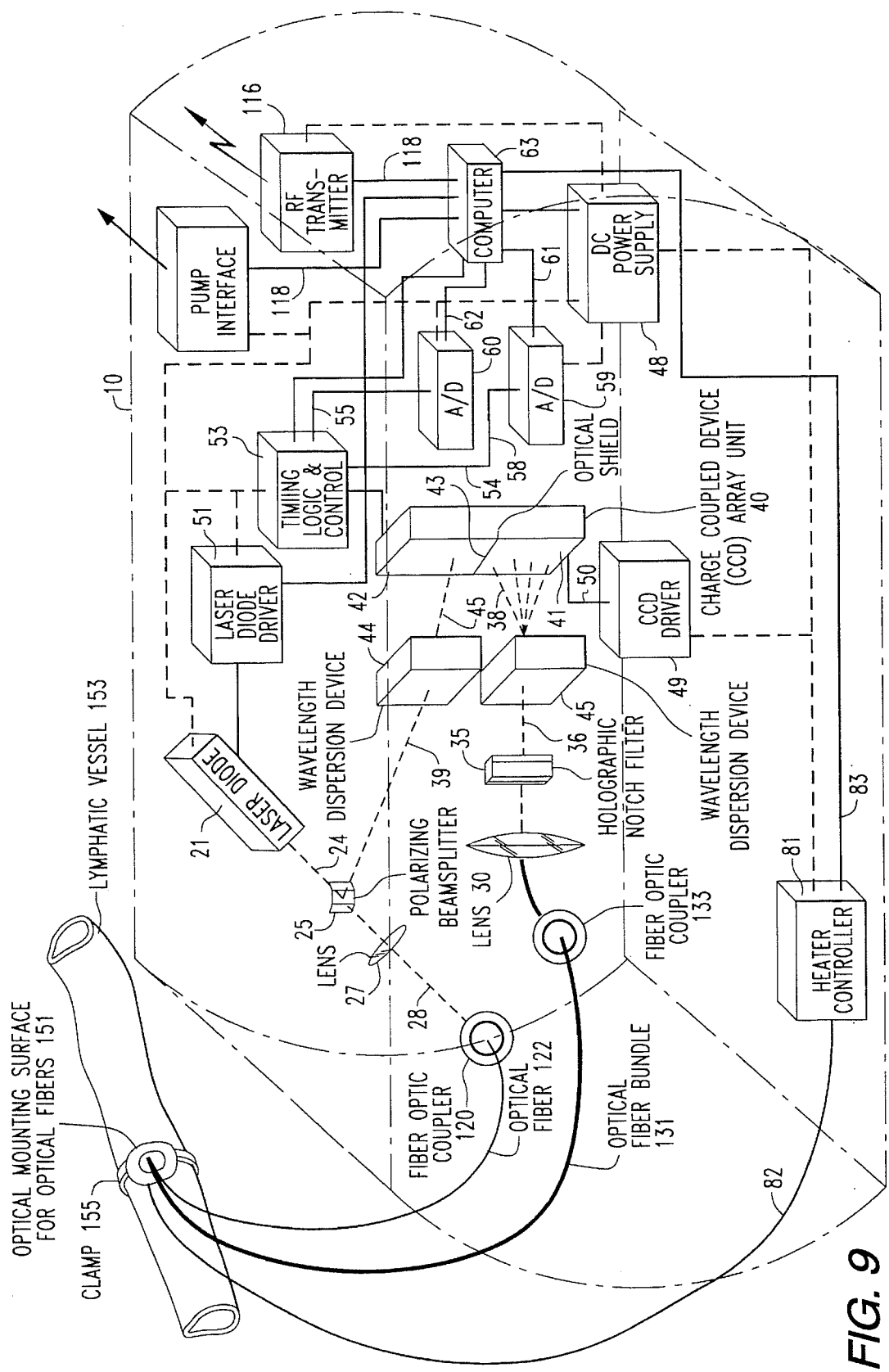
FIG. 9 is a schematic, perspective view of an additional embodiment of the invention that is adapted for body implantation of the device and monitoring biological fluids in a lymphatic vessel of a patient.

FIG. 9 is a schematic, perspective view of an additional embodiment of the invention that is adapted for body implantation of the device and monitoring biological fluids in a lymphatic vessel of a patient using an optical fiber to direct near-infrared source energy to an optical mounting attachment secured around a lymphatic vessel and an optical fiber bundle to gather Raman scattered light. In the configuration of FIG. 9, the fiber mounting fixture 124 for the optical fiber arrangement is mounted to an optical mounting attachment 151 which is secured around lymphatic vessel 153 by way of a clamp member 155.

In each of the embodiments of FIGS. 8 and 9, optical coupling between the irradiating components and scattered light detecting components of the instrument and the medium being monitored is conducted by way of an optical fiber arrangement which extends from the instrument housing to an external fiber coupling element that is attached to a selected tissue location. Where packaging design provides a miniaturized module for the instrument components, the tissue of interest may be located within a passageway, such as may be provided by way of a hinged housing configuration that allows the irradiated medium (e.g. lymphatic vessel) to be encased in an optical viewing bore formed by the closure of respect halves of the housing unit.

Figure 10:
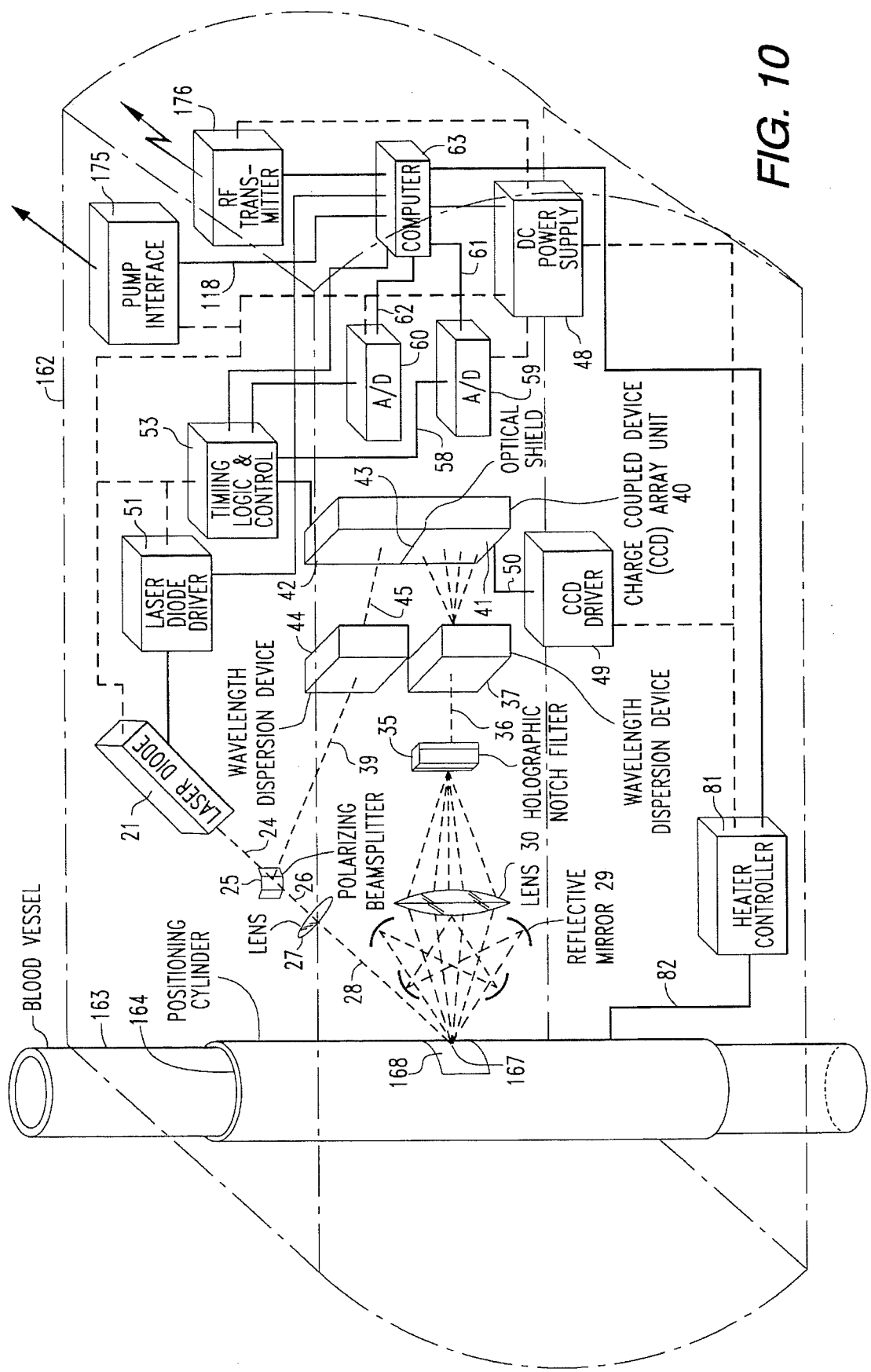
FIG. 10 is a schematic, perspective view of an implantable configuration of the invention that may be applied to in vivo, i.e. attached around a blood vessel, monitoring of glucose and other biological substances.

FIG. 10 is a schematic, perspective view of an implantable configuration of the invention that may be applied to in vivo monitoring of glucose and other biological substances. In the implantable embodiment of FIG. 10, an implantable housing 162 is configured so that it may enclose a blood vessel 163. For this purpose, a positioning cylinder 164 is arranged to engage and cooperate with the blood vessel 163, so that a viewing window 168 is irradiated with the incident laser beam and allows Raman scattering to emanate from location 167, as in the above-described embodiments. A pump interface 175 may be provided so as to allow direct interfacing to an implantable insulin infusion pump (such as one manufactured by MiniMed, Inc.), that may be worn externally by the monitored patient. Also an RF transmitter 176 may be employed to enable external devices to monitor the biological substance levels monitored by the implanted device.

As noted earlier, FIGS. 11, 12 and 13, taken together, are a flowchart of the control mechanism carried out by the control processor of embodiments of the invention for monitoring biological fluids by the use of near-infrared Raman spectroscopy. Connection links among flowlines of the respective Figures are designated at A–F.

Figure 11:
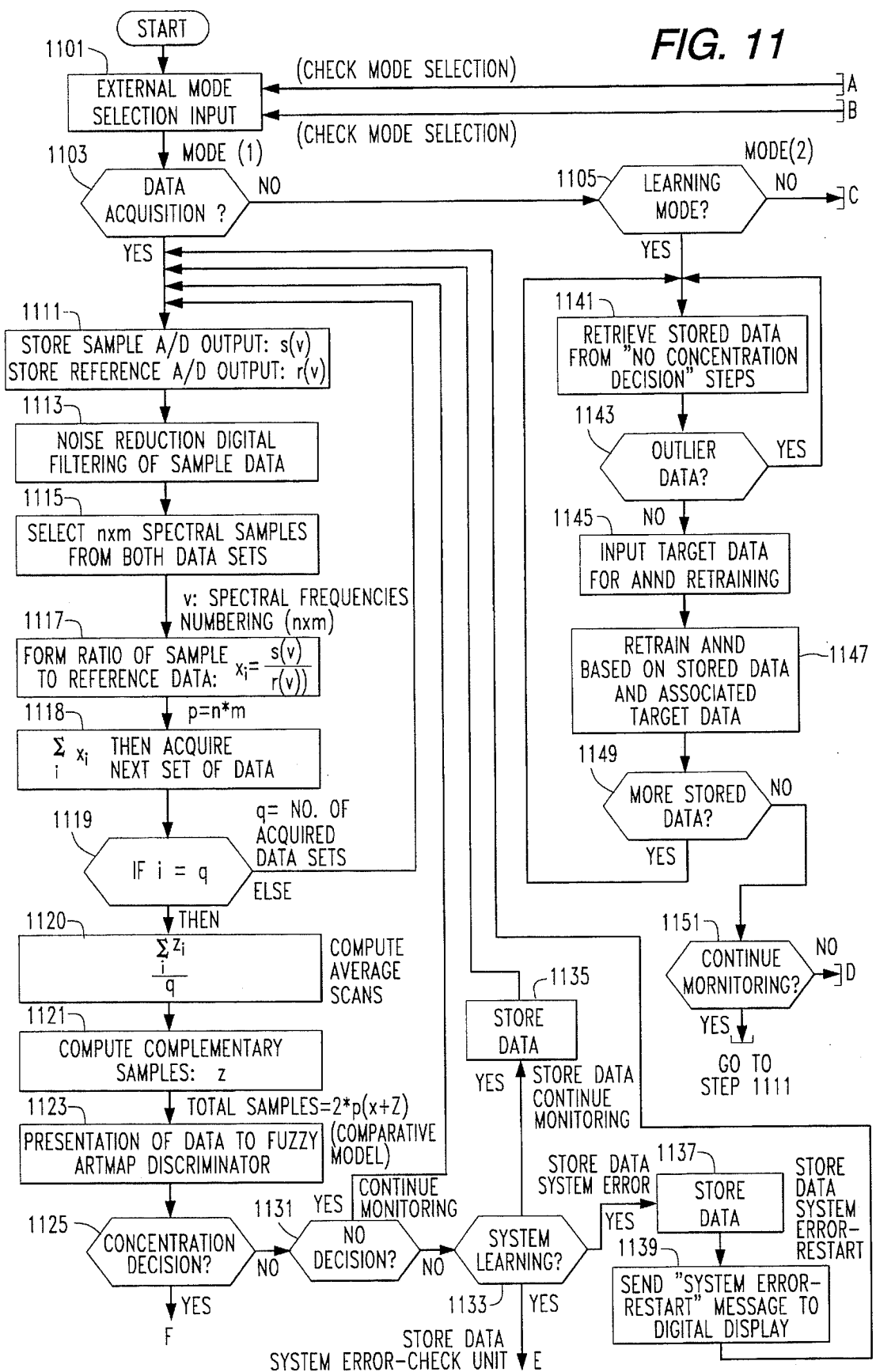
FIGS. 11, 12 and 13, taken together, are a flowchart of the control mechanism carried out by the control processor of embodiments of the invention for monitoring in vitro biological fluids by the use of near-infrared Raman spectroscopy.

As shown in FIG. 11, at the beginning of the routine (START), the processor is user-initiated through an External Mode Selection Input step 1101. The commands employed to select a processor function may be initiated by way of key pad inputs by the user. Three basic modes of operation include: 1)-Data Acquisition query step 1103 (wherein the system monitors concentrations of a biological substance and provides a response which is sent to an attendant digital display unit); 2)-Learning Mode query step 1105 (which requires technical personnel to input calibration target data for enhanced calibration of the calibration [comparative] model; and 3)-Data Transmission Mode query step 1201 (wherein from the monitoring system is sent to a peripheral device, such as an insulin infusion pump; such as diagrammatically illustrated at RF transmitter 116 in FIG. 1, transmitter 116 receiving signals from processor 63 and transmitting data to a peripheral insulin infusion pump).

Data Acquisition Mode (step 1103)

In the Data Acquisition mode, the monitoring system determines concentrations of biological substances (e.g. glucose). The initial step 1111 in the Data Acquisition mode is the storing of data associated with the sample spectrum in the processor memory, the data being the digitized outputs from the analog-to-digital (A-D) converter 60 (FIG. 1). Also stored at step 1111 in the processor memory are data associated with the reference spectrum, which are digitized outputs from the A-D converter 59 (FIG. 1). Timing and logic control unit 53 causes the data to be sequenced according to the outputs from the charge coupled device (CCD) array unit 40 (as controlled by the CCD driver 49) and processor 63 protocols for data storage.

When the entire data sets are stored in processor memory, then, at step 1113, the sample spectral data samples are digital filtered to reduce noise. After digital filtering of the sample data is complete, then at step 1115, p=n×m samples are selected from each of the two data sets stored in memory according to the selection rule previously described. At steps 1117, 1118, 1119 and 1120, ratios of the corresponding spectral frequencies from each data set (i.e., the data sets stored in the processor memory for the sample spectrum and the reference spectrum after selecting p samples from each data set) are formed and then stored in memory, as denoted by ratioed (normalized) spectral values, $\{z_j\}$, for j=1, ... p. At the completion of step 1120, a total of q data sets ("scans") will have been formed and averaged.

After the averaging process is complete, complementary samples, $\bar{z}$, are computed, at step 1121. These samples are computed by calculating the complement of each sample in the set $\{z_j\}$, for j=1, ... p. Thus, each exemplar vector input presented to the Fuzzy ARTMAP artificial neural network discriminator (ANND) is 2*p in length, i.e., the vector $[z\ \bar{z}]^T$ is 2*p×1 in dimension which is presented to the ANND.

Figure 13:
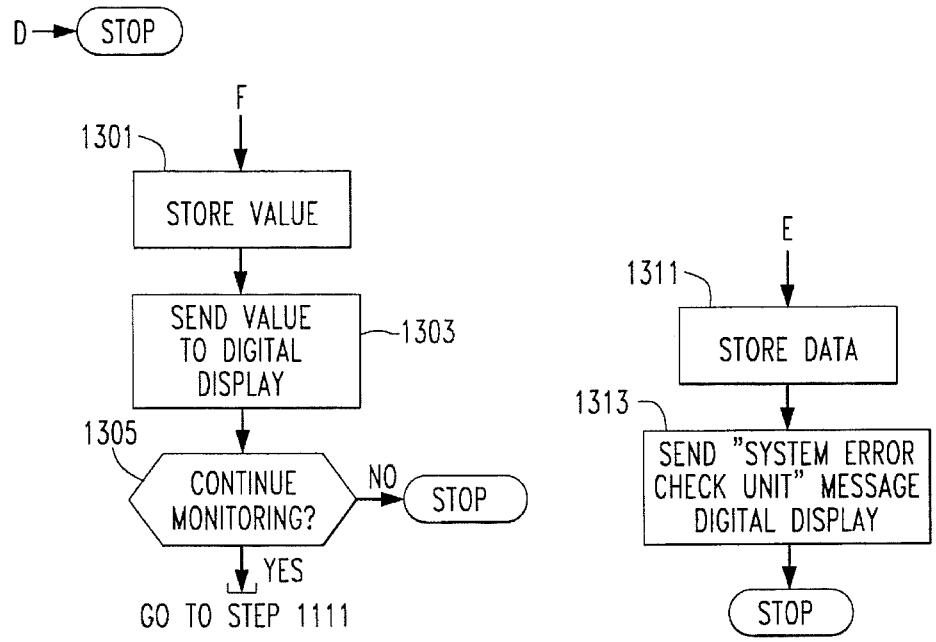

At step 1123, the vector $[z\ \bar{z}]^T$ is presented to the ANND, as shown in FIG. 11, and decision concentration query step 1125 is executed. If the answer to concentration decision step 1125 is YES, the routine follows path F to FIG. 13, wherein, at step 1301, the data are stored and displayed (step 1303) on digital read-out device 66 (FIG. 1). At query step 1305, a determination is made as to whether further monitoring is desired (an option selected by the user by way of External Mode Selection Input step 1101, reference previously). If so, i.e., the answer to query step 1305 is YES, the processor will begin another data acquisition cycle, as shown in FIG. 13 by "looping" to step 1111 in FIG. 11. If the answer to query step 1305 is NO, the process is complete.

If the answer to concentration decision query step 1125 is NO, the routine proceeds to query step 1131, where either a "no decision" is made (the answer to query step 1131 NO, or, if the answer to query step 1131 is YES, monitoring continues (not enough scans were performed and the "continue monitoring" mode is invoked and more scans are accumulated) until a concentration decision is made (the answer to query step 1125 is YES, or a "no decision" is made (the answer to query step 1131 is NO). Where the answer to query step 1131 is NO, the processor switches into the system learning mode, as denoted by query step 1133.

The routine transitions to the system learning mode, in response to the system not being able to make a concentration decision for either of three reasons. First, not enough scans where performed; in this case the "continue monitoring" mode is invoked, after the data are stored in memory at step 1135, and more scans are accumulated. (The only difference between this mode and the previous "continue monitoring" mode is the storage of data in memory). Secondly, if the ANND could not recognize the spectral pattern because the data is an outlier sample, data are saved, i.e., stored in memory, at step 1137, for possible retraining of the ANND. After storing the data, a "System Error—Restart" message is sent to the digital display in step 1139, and data acquisition is restarted at step 1111).

A third possibility in step 1133 involves a determination that the ANND could not recognize the spectral pattern because a system anomaly occurred that the ANND had not been trained to recognize. In this case, as shown by path E to step 1311 in FIG. 13, data are saved in memory and a "System Error—Check Unit" message is sent to the digital display, and the routine terminates, as shown at step 1313. The unit must not be used once this message is displayed, and the monitoring system must be checked out by technical personnel.

Learning Mode (step 1105)

In the Learning Mode (the answer to query step 1105 is YES), two conditions exist. First, the stored data from the "No Decision" query step 1131 is accessed in step 1141 and, in query step 1143, a determination is made as to whether the data are outlier samples. If the answer to step 1143 is YES (i.e. the data are outlier samples), further "off-line" analysis of the data might be necessary; if the answer to query step 1143 is NO, then in steps 1145 and 1147, the data are used to retrain the ANND, and to upgrade the calibration (comparative) model. The proper target data must be supplied along with the associated exemplar vector from the processor memory. In query step 1149 a determination is made as to whether all of the stored data in the processor memory has been retrieved. If there are no more stored data (the answer to query step 1149 is NO), the routine transitions to query step 1151. If there is more stored data (the answer to query step 1149 is YES), the routine loops to step 1141.

In query step 1151 a determination is made as to whether monitoring can continue. Monitoring can continue by returning to step 1111, by selecting the Data Acquisition mode through the External Mode Selection Input step 1101, or the unit can be shut off via path D.

Data Transmission Mode (step 1201)

In the Data Transmission mode (shown by step 1201 in FIG. 12), data stored in the processor's memory can be sent to external devices, such as an insulin infusion pump or other devices. If the RF link is to be used to transmit data to an insulin infusion pump (the answer to a query step 1203 is YES) then, in step 1205, an RF Transmitter Enable signal is sent to the RF Transmitter 116 shown in FIG. 1. Processor 63 transmits an enable signal and appropriate information by way of the data link 118 which couples the information to RF Transmitter 116. In query step 1207 a decision is made as to whether monitoring can continue by selecting the Data Acquisition mode (the answer to step 1207 is YES, through the External Mode Selection Input step 1101, or the unit can be shut off (stopped).

Other devices can receive data from the monitoring system's processor, as denoted by query step 1211. The sub-routine for this function is the same as that used as in the case of the RF Transmitter Enable query step 1203, described above. If the data are to be transmitted to another device (the answer to a query step 1211 is YES) then, in step 1213, the data are retrieved and transmitted to a prescribed external device.

For example, the data may be retrieved and transmitted to, such as the configuration shown in FIG. 10, described above, where pump interface 175 is coupled in a direct link to an implanted insulin infusion pump. In this application, processor 63 outputs control signals by way of a data link to the pump interface unit in the implanted monitoring system.

Figure 12:
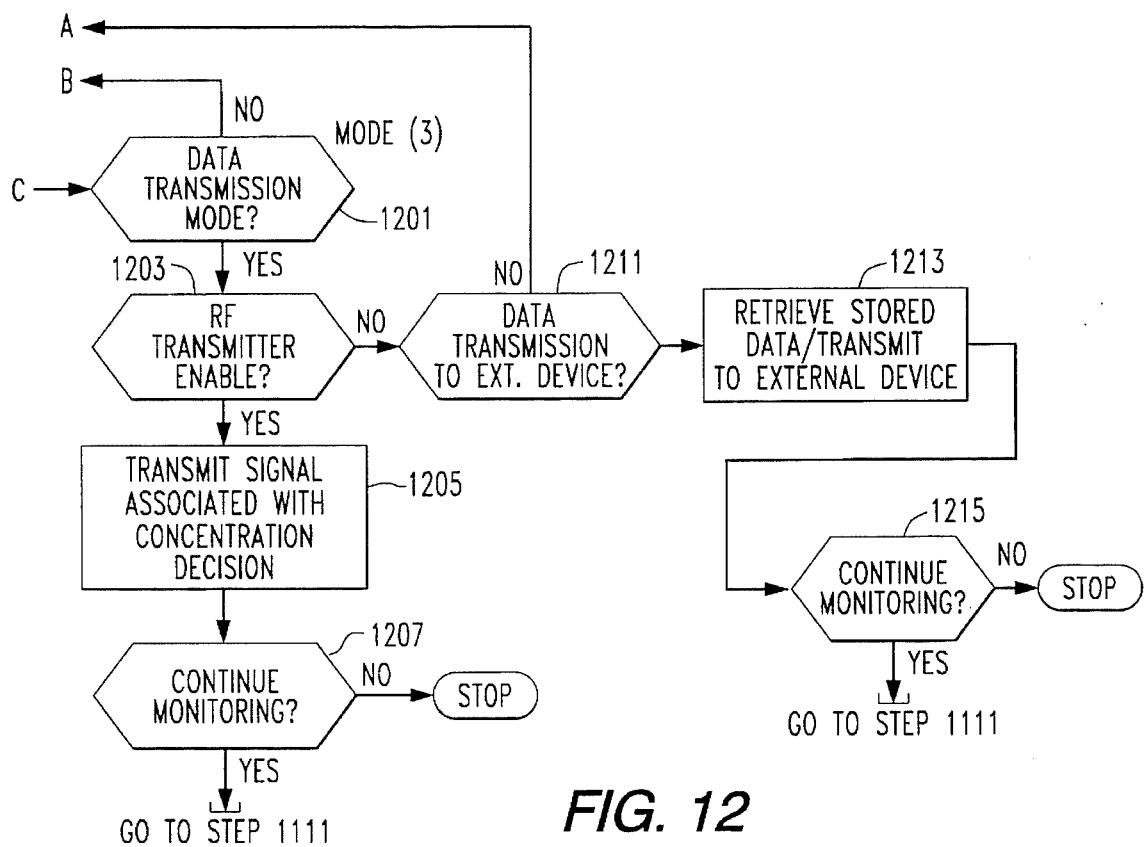

As shown in FIG. 12, a continue monitoring query step 1215 allows monitoring to proceed (1215 is YES), through the External Mode Selection Input step 1101, or the unit can be shut off (stopped). Dual self checking in the data transmission mode is performed at query steps 1201 and 1211 via paths A and B, respectively. This is to insure that data are not transmitted to any device unless it is verified by the external mode selection input step 1101, in the event that a conflict of function commands occurs.

As will be appreciated from the foregoing description, the Raman scattering mechanism of the present invention successfully overcomes the above-described shortcomings of the prior art by providing a device which is highly robust, non-invasive, yields direct concentration measurements, and is continuous or near continuous in measuring concentrations of glucose (for the treatment of diabetes mellitus) and/or other biological substances, including those which experience physiological perturbations as a function of time and from one individual to another. An important aspect of the invention is the fact that it employs a constant-baseline comparative model, in particular a fuzzy ARTMAP artificial neural network discriminator that is robust with respect to molecular interactions of other biological analytes with the substance under analysis (e.g. glucose), when the interfering biological analytes are present in varying amounts. The invention is also capable of providing a constant-baseline comparative model that is capable of identifying outlier samples, and either rejects the data as an anomaly, or provides a system response that indicates possible inclusion of this sample in the comparative model. In the latter case, the sample may have been a condition not previously considered in the model calibration process, which is associated with a physiological condition consistent with normal metabolic conditions. Advantageously, Raman spectroscopy is equally as specific as FTIR (Fourier Transform Infrared) spectroscopy, but is better adapted to aqueous based analyses. Acquisition times are about the same as those for FTIR. The use of fiber optic probes is better suited with the Raman spectroscopy embodiments described above than with FTIR, since fiber optic cables for infrared wavelengths are extremely expensive and fragile.

While we have shown and described several embodiments in accordance with the present invention, it is to be understood that the same is not limited thereto but is susceptible to numerous changes and modifications as known to a person skilled in the art, and we therefore do not wish to be limited to the details shown and described herein but intend to cover all such changes and modifications as are obvious to one of ordinary skill in the art.

What is claimed:

1. A method of non-invasively deriving a measure of the concentration of glucose in a human body fluid comprising the steps of:
    (a) irradiating a human body tissue containing said human body fluid with monochromatic light in the near infrared spectral region emitted by a monochromatic light source, thereby causing said glucose within the irradiated human body tissue to produce Raman scattering of said monochromatic light into multiple, spatially separated, frequency shifted wavelength components associated with molecular characteristics of said glucose;
    (b) tracking variations in light emitted by said monochromatic light source;
    (c) directing said multiple, spatially separated, frequency shifted wavelength components resulting from said Raman scattering through a holographic notch filter, which removes the Rayleigh component of scattered light, onto a photosensitive detector, which produces electrical output signals representative of said multiple, spatially separated, frequency shifted wavelength components associated with molecular characteristics of said glucose;
    (d) generating ratio signals representative of the ratios of said electrical output signals representative of said multiple, spatially separated, frequency shifted wavelength components resulting from said Raman scattering produced in step (c) to variations in monochromatic light emitted by said monochromatic light source tracked in step (b), so as to eliminate effects of variations of said monochromatic light source; and
    (e) processing said ratio signals by means of a fuzzy adaptive resonance theory artificial neural network discriminator that has been trained with a plurality of training exemplars, corresponding to scattered light components representative of different concentrations of glucose, and which is robust to a human body fluid sample not previously encountered, and quantitatively deriving therefrom concentrations of said glucose in human body fluid based upon the spectral intensities of detected wavelengths of said spatially separated, frequency shifted wavelength components.

2. An apparatus for non-invasively deriving a measure of the concentration of glucose in a human body fluid comprising:
    a monochromatic light source which emits monochromatic light in the near infrared spectral region, and irradiates
    human body tissue containing said human body fluid with said monochromatic light, thereby causing glucose within the irradiated human body tissue to produce Raman scattering of said monochromatic light into multiple, spatially separated, frequency shifted wavelength components representative of molecular characteristics of said glucose;
    a holographic notch filter;
    optical elements which direct said multiple, spatially separated, frequency shifted wavelength components resulting from said Raman scattering through said holographic notch filter, which removes the Rayleigh component of scattered light incident thereon;

a first photosensitive detector device, which is disposed to receive light passing through said holographic notch filter and produces electrical output signals representative of said multiple, spatially separated, frequency shifted wavelength components representative of molecular characteristics of said glucose;

a second photosensitive detector device, which is disposed to receive monochromatic light emitted by said monochromatic light source and produces signals representative of variations in light emitted by said monochromatic light source;

a ratio signal processor, which is coupled to receive said signals representative of variations in light emitted by said monochromatic light source and said electrical output signals, and which generates ratio signals representative of the ratios of said electrical output signals representative of said multiple, spatially separated, frequency shifted wavelength components resulting from said Raman scattering to variations in monochromatic light emitted by said monochromatic light source, so as to eliminate effects of variations of said monochromatic light source; and a fuzzy adaptive resonance theory artificial neural network discriminator that has been trained with a plurality of training exemplars, corresponding to scattered light components representative of different concentrations of glucose, and which is robust to a human body fluid sample not previously encountered, said fuzzy adaptive resonance theory artificial neural network processing said ratio signals and quantitatively deriving therefrom concentrations of said glucose in human body fluid based upon spectral intensities of the detected wavelengths of said spatially separated, frequency shifted wavelength components.

* * * * *